United States Patent [19]

Davison et al.

[11] Patent Number: 5,447,513
[45] Date of Patent: Sep. 5, 1995

[54] ENDOSCOPIC LIGATION AND DIVISION INSTRUMENT

[75] Inventors: Mark A. Davison; William D. Kelly; Rudolph H. Nobis, all of Mason; Jerome E. Reckelhoff, Blue Ash, all of Ohio

[73] Assignee: Ethicon, Inc., Somerville, N.J.

[21] Appl. No.: 113,031

[22] Filed: Aug. 27, 1993

Related U.S. Application Data

[63] Continuation of Ser. No. 879,676, May 6, 1992, abandoned.

[51] Int. Cl.⁶ .............................................. A61B 17/00
[52] U.S. Cl. .................................. 606/143; 606/139; 606/142; 227/901
[58] Field of Search ............... 606/139, 142, 143, 120, 606/126, 205, 207, 208; 227/175, 176, 177–182, 19, 901

[56] References Cited

U.S. PATENT DOCUMENTS

| | | | |
|---|---|---|---|
| 2,316,297 | 4/1943 | Southerland et al. | 606/139 |
| 3,484,940 | 12/1969 | Zell, Jr. | |
| 3,889,683 | 6/1975 | Kapitanov et al. | 606/143 |
| 4,349,028 | 9/1982 | Green | 606/143 |
| 4,569,346 | 2/1986 | Poirier | |
| 4,616,650 | 10/1986 | Green et al. | 606/143 |
| 4,674,501 | 6/1987 | Greenberg | |
| 4,784,137 | 11/1988 | Kulik et al. | 227/177 |
| 5,040,715 | 8/1991 | Green et al. | 227/176 |
| 5,084,057 | 1/1992 | Green et al. | |
| 5,100,420 | 3/1992 | Green et al. | |
| 5,104,394 | 4/1992 | Knopfler | |
| 5,147,373 | 9/1992 | Ferzli | 606/207 |
| 5,171,247 | 12/1992 | Hughett et al. | |
| 5,171,249 | 12/1992 | Stefanchik et al. | |
| 5,171,250 | 12/1992 | Yoon | 606/142 |
| 5,176,695 | 1/1993 | Dulebohn | |
| 5,190,560 | 3/1993 | Woods et al. | 606/143 |

OTHER PUBLICATIONS

Brochure by MTI Corporation, for precision arthroscopic instruments and multi-purpose knives.
Advertisement by DaVinci Medical for a hook cutter, appearing in Surgical Laparoscopy and Endoscopy, vol. 1, No. 3 (1991), Raven Press.

*Primary Examiner*—Stephen C. Pellegrino
*Assistant Examiner*—Jeffrey A. Schmidt
*Attorney, Agent, or Firm*—Emil R. Skula

[57] ABSTRACT

An endoscopic surgical apparatus capable of ligation and division. The apparatus has a frame and a tubular shaft attached to said frame. Also attached to the frame is a handle. The apparatus has ligating means and cutting means. Actuation means are mounted to the apparatus for actuating both the ligating means and the cutting means. The apparatus has a clutch means capable of enabling the actuating means to switch between a first mode for actuating the ligating means and a second mode for actuating the cutting means. The cutting means is preferably an extendable J-hook and blade assembly. The cutting means and ligating means are preferably rotatable with respect to the frame. The ligation and division apparatus may be used to ligate and cut blood vessels or tissue in a mammalian body cavity during a surgical procedure.

36 Claims, 15 Drawing Sheets

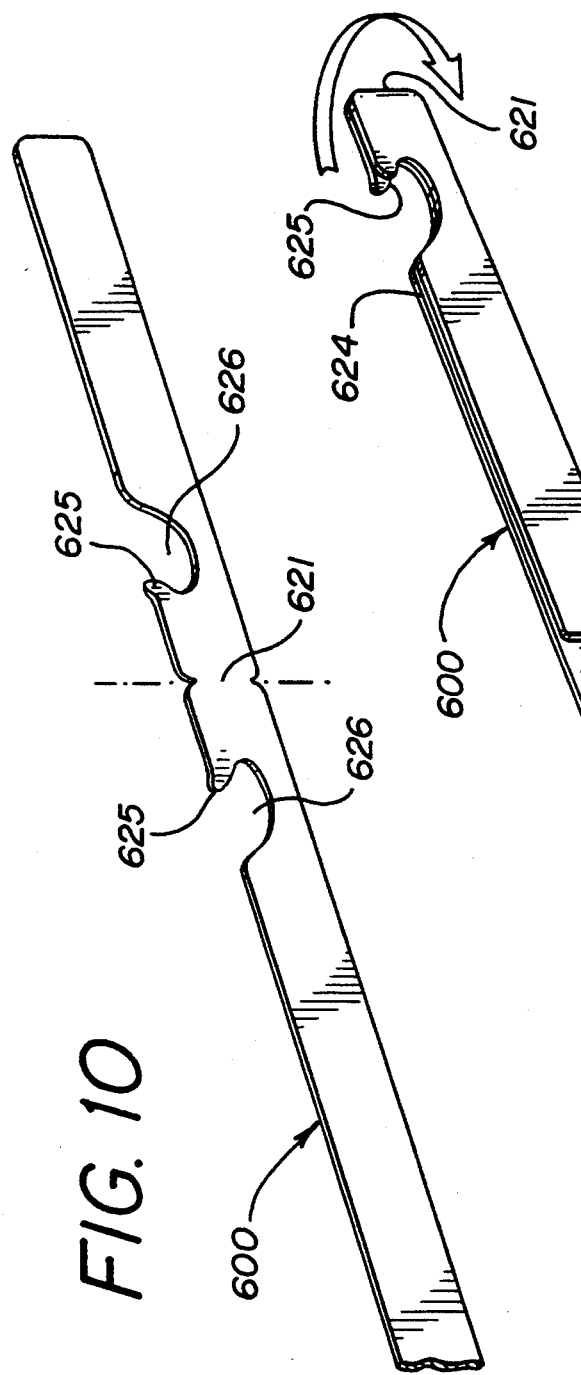
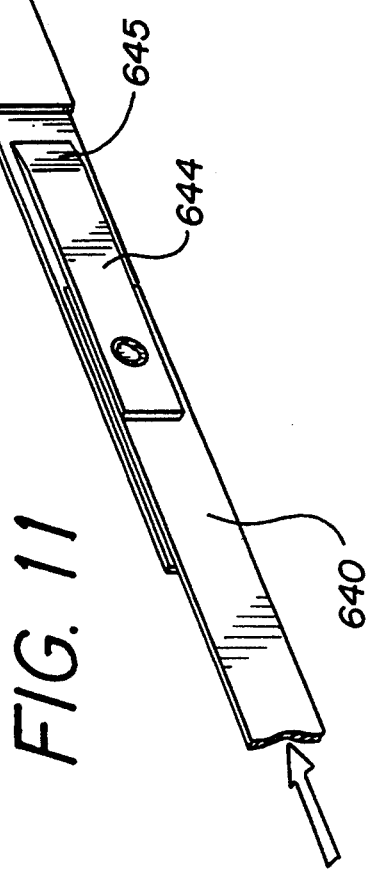
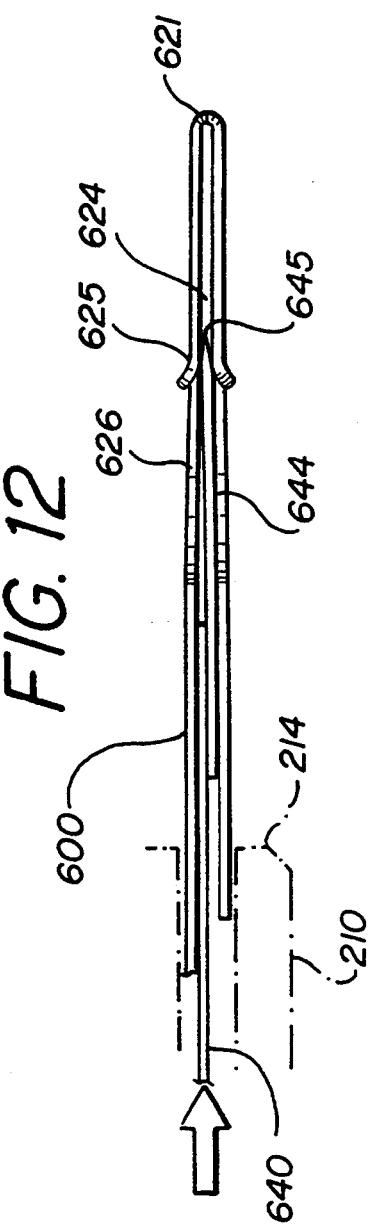
FIG. 10
FIG. 11
FIG. 12

ENDOSCOPIC LIGATION AND DIVISION INSTRUMENT

This is a continuation of application Ser. No. 07/879,676, filed May 6, 1992 now abandoned.

TECHNICAL FIELD

The field of art to which this invention relates is surgical instrumentation, in particular, endoscopic surgical instruments.

BACKGROUND OF THE INVENTION

Endoscopic surgical techniques have become widely accepted among the medical community. There are numerous benefits associated with the use of endoscopic surgical techniques rather than conventional open surgical techniques. It has been found that avenues for infection are greatly reduced and the patient typically has a shortened post-operative recuperative period. It is not unusual for the postoperative period to be shortened from weeks to several days, and, out patient endoscopic surgery is becoming evermore typical. The term endoscopic as used herein is defined to include endoscopic, laparoscopic, arthroscopic and thorascopic.

In a typical endoscopic surgical procedure, the abdominal cavity of a mammal is typically insufflated with a sterile gas, such as carbon dioxide, in order to provide increased maneuvering room within the body cavity for endoscopic instruments. Then, conventional trocars are inserted into the patients body cavity through the surrounding skin, tissue, and musculature. A conventional trocar typically consists of a trocar cannula which houses an elongated trocar obturator. Trocar obturators typically have a piercing point, although other types of obturators are also available. Once the trocar has been positioned within the body cavity, proximal to the target surgical site, the trocar obturator is removed leaving the trocar cannula as a pathway to the body cavity. The surgeon will place various types of endoscopic surgical instruments through the trocar in order to access the target surgical site where the surgical procedure will be performed. Examples of endoscopic instruments include ligating clip appliers, electrosurgical instruments, endoscopes, tissue graspers, needle graspers, cannulas, tissue manipulators, and the like.

Although endosurgical procedures and techniques offer many advantages, there are some deficiencies associated with these procedures and techniques. In particular, when the surgeon is operating using endoscopic surgical procedures, he is typically using an endoscope which is positioned within the body cavity through a trocar. The endoscope is typically connected to a video camera and the output from the video camera is displayed on a video monitor. The surgeon typically views the display on the video monitor as he manipulates instruments within the body cavity to access the target surgical site and perform the actual surgical procedures. The video display only provides the surgeon with two-dimensional input and there is a consequent loss of depth perception. This lack of depth perception may result in the surgeon overshooting or undershooting the target surgical site as he attempts to position his endoscopic instruments within the body cavity.

When ligating a blood vessel, the surgeon typically positions the endoscopic ligating clip applier around a blood vessel and applies clips to either side of an intended cut. Then the surgeon removes the ligating clip applier from the patient's body cavity and inserts a cutting device such as endoscopic scissors. Often the maneuvering of the endoscopic scissors to the ligated blood vessel is time consuming and potentially hazardous to the patient since the surgeon is attempting to maneuver an instrument in three dimensional space with only two-dimensional visual input. If appropriate care is not taken, it is possible for the surgeon to accidentally cut or puncture vessels or organs as the surgeon attempts to position the scissors about the ligated blood vessel.

What is needed in this art is an endoscopic surgical instrument which would apply a ligating clip to a blood vessel or tissue and which would also have the capability of cutting the blood vessel or tissue, thereby eliminating the need to withdraw a ligating clip applier and insert a separate cutting instrument.

SUMMARY OF THE INVENTION

It is an object of the present invention to provide an endoscopic surgical instrument which can both apply ligating clips to a blood vessel or tissue, and cut the blood vessel or tissue.

It is yet another object of the present invention to provide an endoscopic instrument capable of both applying ligating clips to a blood vessel or tissue and cutting the blood vessel or tissue, wherein ligation and cutting are controlled by a single actuating trigger.

It is yet another object of the present invention to provide a cutting means having a cutting blade for the above-described endoscopic ligation and cutting instrument wherein the cutting blade is not exposed or actuated until the blood vessel or tissue is engaged by the cutting means.

Accordingly, an endoscopic surgical apparatus is disclosed. The endoscopic surgical apparatus is capable of ligation and division. The apparatus has a frame and a tubular shaft attached to said frame. Also attached to the frame is a handle. The apparatus has ligating means and cutting means. Actuation means are mounted to the apparatus for actuating both the ligating means and the cutting means. The apparatus has a clutch means capable of enabling the actuating means to switch between a first mode for actuating the ligating means and a second mode for actuating the cutting means. The cutting means is preferably an extendable J-hook and blade assembly. The cutting means and ligating means are preferably rotatable with respect to the frame. The ligation and division apparatus may be used to ligate and cut blood vessels or tissue in a mammalian body cavity during a surgical procedure. The apparatus preferably has feed means attached to said frame for feeding a plurality of clips to the ligating means.

Yet another aspect of the present invention is a method of using the above-described apparatus to ligate and cut tissue or blood vessels.

Other features and advantages of the invention will become more apparent from the following description and accompanying drawings.

BRIEF DESCRIPTION OF THE DRAWINGS

FIG. 10 is a perspective view of the distal end of the J-hook part of the cutting means prior to forming the isolation hook and track.

FIG. 11 is a perspective view of the assembled cutting means.

FIG. 12 is a top plan view of the cutting means of FIG. 11 after the cutting blade has been pushed through the isolation hook.

FIG. 17A is a schematic partial top plan view of the disengagement means of the trigger assembly shown in a first position.

FIG. 18A is a schematic partial top plan view of the disengagement means of the trigger assembly shown in a second position.

BEST MODE FOR CARRYING OUT THE INVENTION

Figure 1:
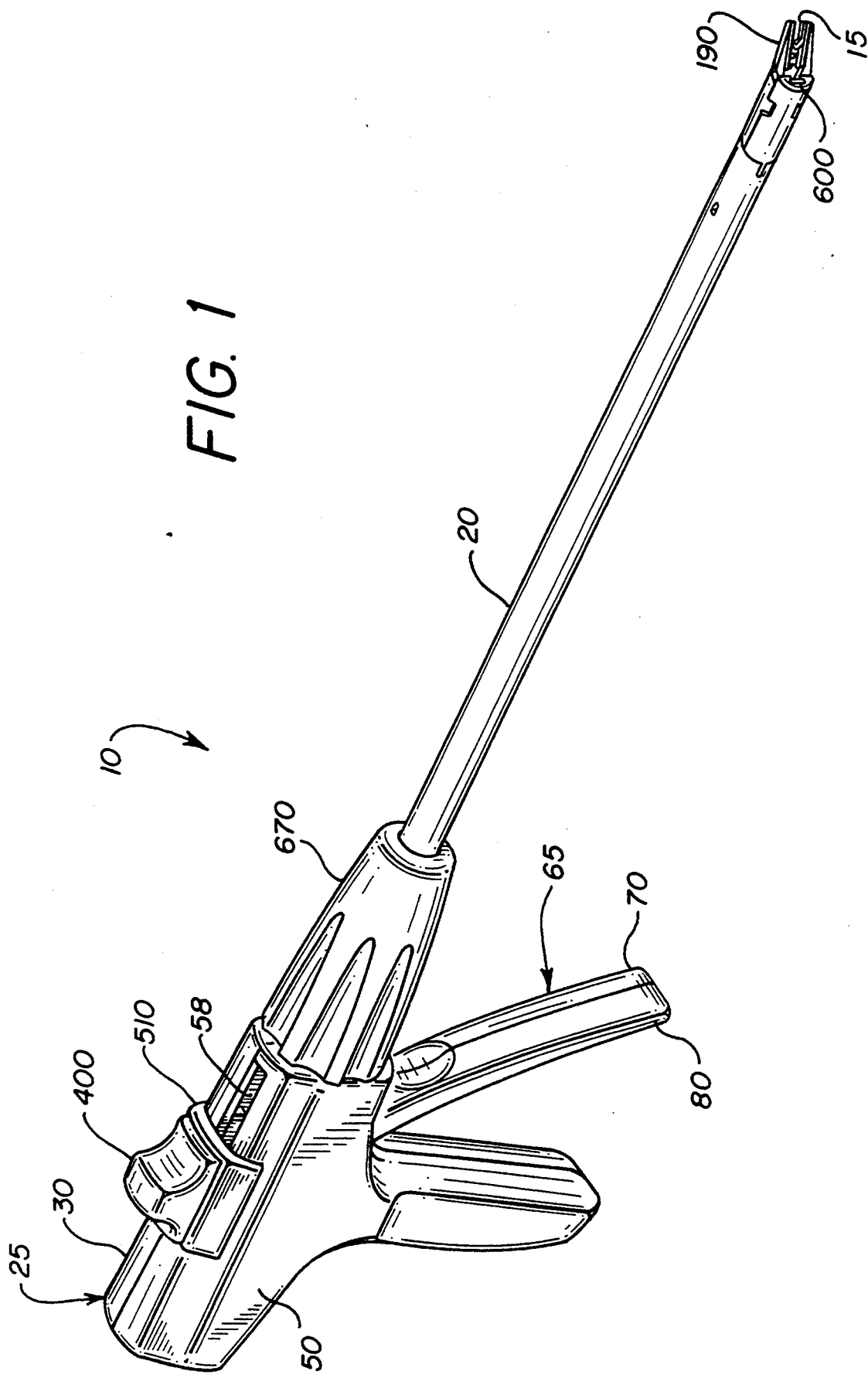
FIG. 1 is a perspective view of the endoscopic ligation and division apparatus of the present invention.
Figure 5:
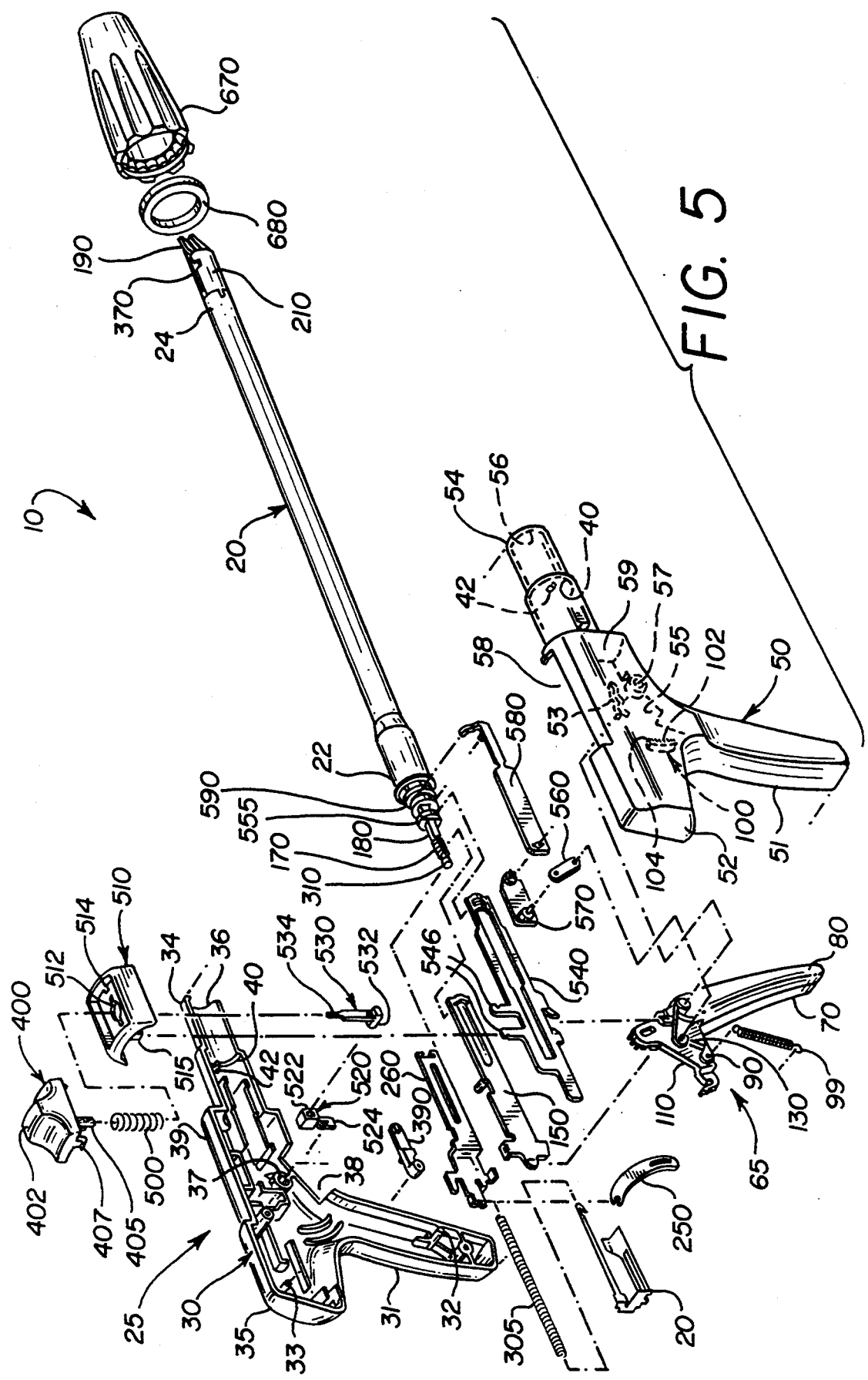
FIG. 5 is an exploded perspective view of the ligation and division apparatus of FIG. 1.

The endoscopic ligation and division apparatus 10 is seen in FIG. 1, and FIG. 5. The endoscopic ligation and division apparatus 10 is used to apply ligating clips 15 to body tissues and blood vessels including arteries, veins, capillaries, arterioles, mesentery, nerves, ducts, tubular passages and the like. The apparatus 10 is also used to cut said tissue or blood vessels, typically after ligating clips have been applied. The endoscopic ligation and division apparatus 10 is seen to have a hollow frame 25 consisting of left frame 30 and right frame 50. As seen in FIG. 5, left frame 30 is a hollow member having downwardly extending handle grip portion 31 which contains trigger spring pin 32. The frame 30 has an elongate housing portion 39 having proximal end 35 and distal end 34. Distal end 34 has semicircular aperture 36 for receiving the proximal end 22 of support tube 20. Located within the proximal end 35 of the left frame 30 is the precock trigger pin 33. The pivot journal 37 is centrally located within the left frame 30, adjacent to trigger aperture 38 and extends from the interior wall of frame 30. Trigger aperture 38 is an elongate aperture extending through the wall of frame 30 adjacent to the top of the handle grip 31. Trigger aperture 38 receives trigger assembly 65.

The right frame 50 is a hollow member which mates with the left frame 30 to form hollow frame 25. The right frame 50 has handle grip 51 extending downwardly from proximal end 52 of the right frame. The right frame 50 has an elongate housing portion 59 having proximal end 52 and distal end 54 which contains semicircular aperture 56 for receiving the proximal end 22 of support tube 20. The right frame 50 contains internal pivot journal 57 adjacent to trigger aperture 55. The pivot journal 57 extends from the interior wall of right frame 50. Trigger aperture 55 is an elongate aperture extending through the wall of frame 50 adjacent to the top of the handle 51. Trigger aperture 55 also receives trigger assembly 65.

Centrally located at the top of the frame 50 is the aperture 58 for mounting the button 400 and the base 510. As will be discussed herein, the button 400 and the base 510 are part of the cutter extension means. A cutting track groove 53 is contained within the frame 50 above the pivot journal 57. The proximal pin 572 of the plunger link 570 is engaged therein. The tooth rack 100 is seen to extend from the inside wall of frame 50. The tooth rack 100 is located at the top of the handle 51 and extends into the lower section of housing 59. The tooth rack 100 is engaged by the pawl 117 of the former link 110. The tooth rack 100 consists of a series of teeth 102 and a top lever member 104. The tooth rack 100 and the pawl 117 act together to form an anti-backup mechanism which prevents the jaw assembly 190 from releasing a partially formed clip 15. The left frame 30 and the right frame 50 are assembled to form hollow frame 25 using conventional methods including ultrasonic welding, bonding with conventional adhesives, fastening with conventional mechanical fasteners, and the like. It is particularly preferred to use ultrasonic welding to join left frame 30 to right frame 50.

Figure 6:
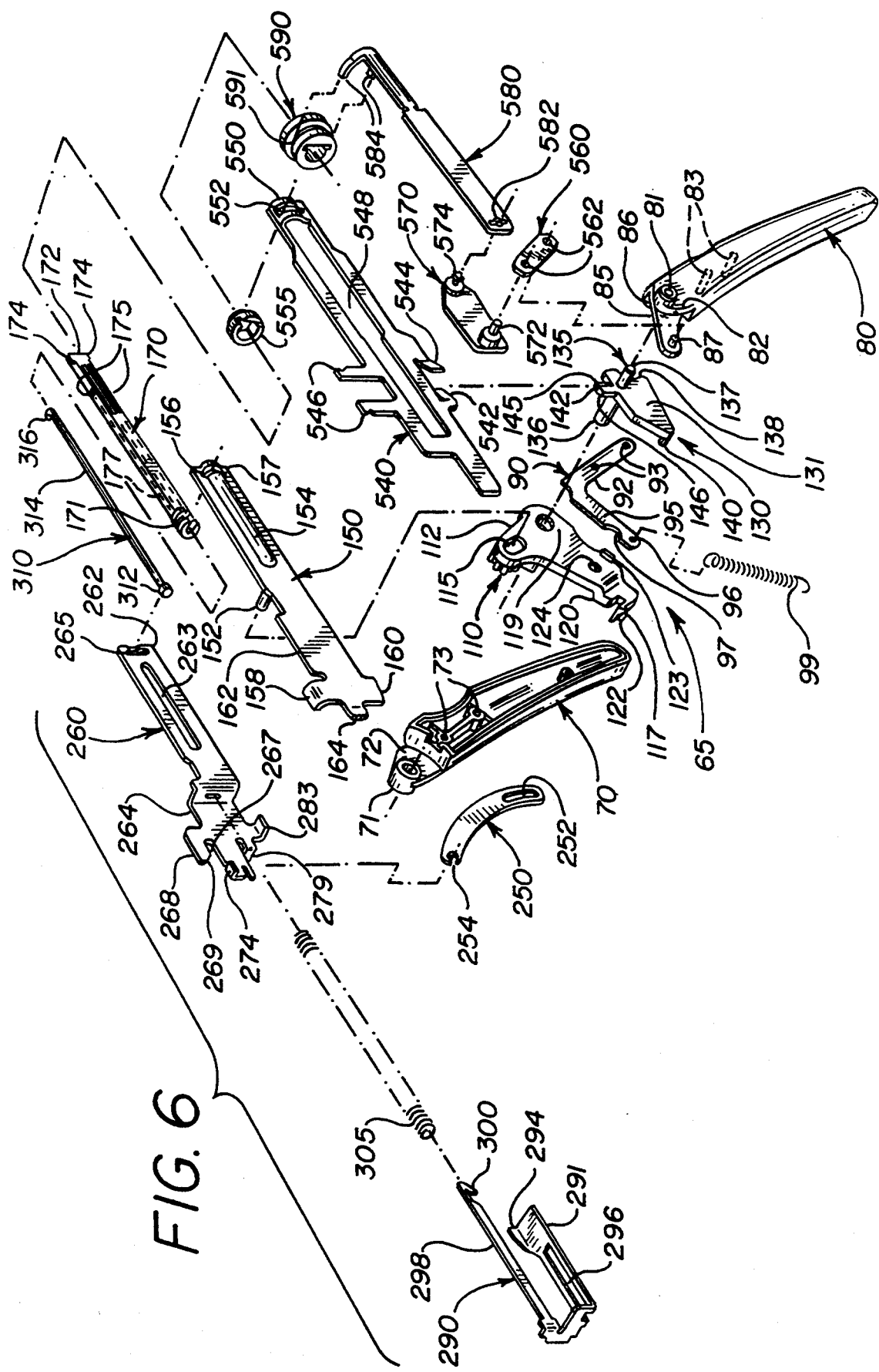
FIG. 6 is a further exploded perspective view of the trigger assembly and associated parts.

Referring now to FIG. 6, the trigger assembly 65 is seen to comprise the left trigger 70, the right trigger 80, the trigger plate 90, the former link 110 and the clutch 130. The left trigger 70 is an elongate hollow member having offset member 72 extending from the top thereof. Pivot bearing 71 extends outwardly from offset member 72. Pivot bearing 71 is mounted in pivot journal 37 of left frame 30. Left trigger 70 has pin receiving bosses 73 for mounting trigger plate 90. Right trigger 80 is an elongate, hollow member which mates with left trigger 70. Right trigger 80 also has offset member 82 extending from the top thereof. Right trigger 80 is seen to have pivot bearing 81 extending outwardly from offset member 82. Pivot bearing 81 is mounted in pivot journal 57 of right handle 50. Extending from the top of offset member 82 is the upwardly extending trigger link 85. Mounting posts 83 are seen to extend from the interior of right trigger 80 for mounting trigger plate 90. Trigger pins 83 and bosses 73 also serve to align the right trigger 80 and the left trigger 70 during assembly. Drive rib 86 is seen to extend from the top of right trigger 80 adjacent to the bottom of offset member 82. Drive rib 86 engages face 138 of clutch 130.

The trigger plate 90 is seen to have plate leg 92 and plate leg 95. The plate legs 92 and 95 are positioned substantially perpendicular with respect to each other. The plate leg 92 has mounting holes 93 therethrough for mounting into right trigger 80 at mounting posts 83. At the proximal end of plate leg 95 is located hole 96 for mounting the distal end of trigger spring 99. Trigger spring 99 is mounted at its proximal end to trigger spring pin 32, and at its distal end in hole 96 of plate leg 95. The plate leg 95 also has semi-circular slot 97 cut into the top side thereof for clearance of engagement pin 140. The former link 110 is an irregularly shaped member having, at its distal end, upwardly extending leg 112 containing upper drive slot 115. Located below drive slot 115 is the circular hole 119 for engaging shaft 136 of pivot axle 135. At the proximal end of the former link 110 is the anti-backup pawl 117 which engages tooth rack 100 in handle 50. Proximal to the hole 119 is the engagement hole 124 for engaging the engagement pin 140 of the clutch 130. The proximal end of former link 110 is offset to form the drive link 120. Extending outwardly from drive link 120 is pin 122. Below engagement hole 124 is former link return tab 123. Former link return tab 123 serves to return former link 110 to its at-rest position after actuation of the ligating mechanism. Former link return tab 123 is engaged by trigger plate leg 95 during release of trigger assembly 65, thereby returning former link 110 to the at-rest position and serves to re-align engagement hole 124 of former link 110 with engagement pin 140 of clutch 130.

Referring to FIG. 6, FIG. 17A and FIG. 18A, the clutch 130 is seen to be a plate-like member 131 having a pivot axle 135. The pivot axle 135 consists of a left shaft member 136 extending from one face of the plate-like member 131 and a right shaft member 137 extending oppositely from the other face of the plate-like member 131. Extending from the top of the plate-like member 131 of clutch 130 is the cam member 142 which has engagement cam surface 145(on the right hand side of member 142) and disengagement cam surface 146 (on the left hand side of member 142). An engagement pin 140 is seen to extend outwardly from the lower proximal end of the clutch 130. The clutch 130 is also seen to have offset face 138 for engaging driving rib 86 of right trigger 80.

The trigger assembly 65 is assembled by initially inserting the clutch 130 into the right trigger 80 by inserting the left shaft member 137 of pivot axle 135 into pivot bearing 81 of right trigger 80. Then, the trigger plate 90 is installed by lining up mounting holes 93 with mounting pins 83 and displacing the holes 93 over the pins 83 so that the pins 83 extend through the holes 93. Then the former link 110 is mounted on top of the clutch 130 and trigger plate 90 so that the left shaft member 136 of pivot axle 135 is inserted through hole 119 of the former link 110. The left trigger 70 is then mounted to right trigger 80 such that the shaft member 136 is inserted into pivot bearing 71 of left trigger 70. Also, the pin receiving bosses 73 in left trigger 70 receive and engage mounting pins 83. The left trigger 70 is secured to the right trigger 80 by methods known in the art including ultrasonic welding, bonding with conventional adhesives, fastening with conventional mechanical fasteners, and the like. Pivot bearing 71 and pivot bearing 81 of trigger assembly 65 are mounted, respectively, in pivot journal 37 of left frame 30 and pivot journal 57 of right frame 50. It can be seen that the clutch 130 is slidably mounted, laterally, in the pivot bearings 71 and 81 so that engagement pin 140 can slide, laterally, into and out of engagement hole 124 of former link 110. Further it can be seen that the clutch 130, the former link 110 and the plate leg 95 are partially contained between offset members 72 and 82. Driving rib 86 of right trigger 80 engages face 138 of clutch 130 such that rotation of trigger assembly 65 causes rotation of the clutch 130.

Figure 15:
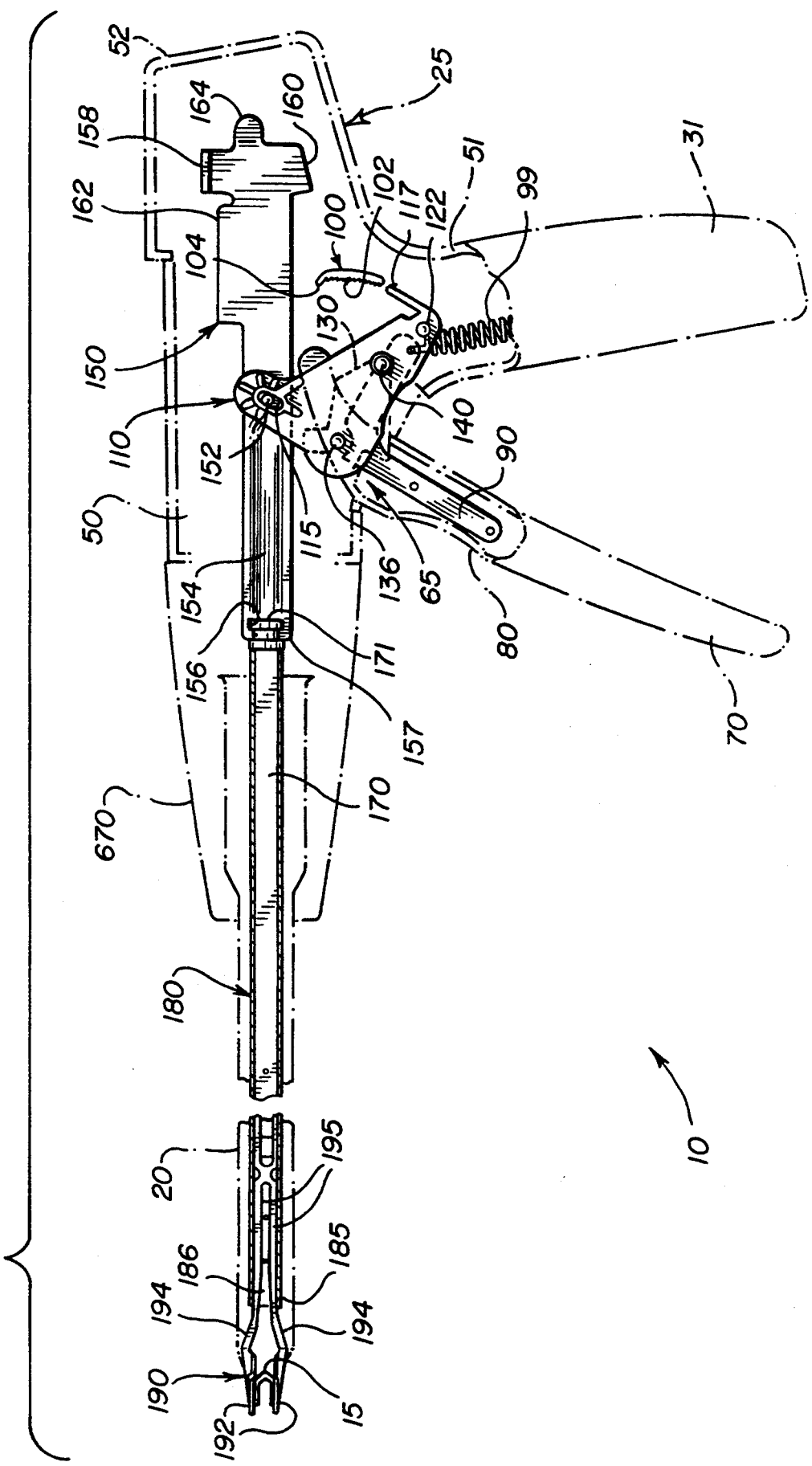
FIG. 15 is a side elevational view of the apparatus showing the ligation clip forming system at rest wherein certain parts have been omitted for clarity.
Figure 16:
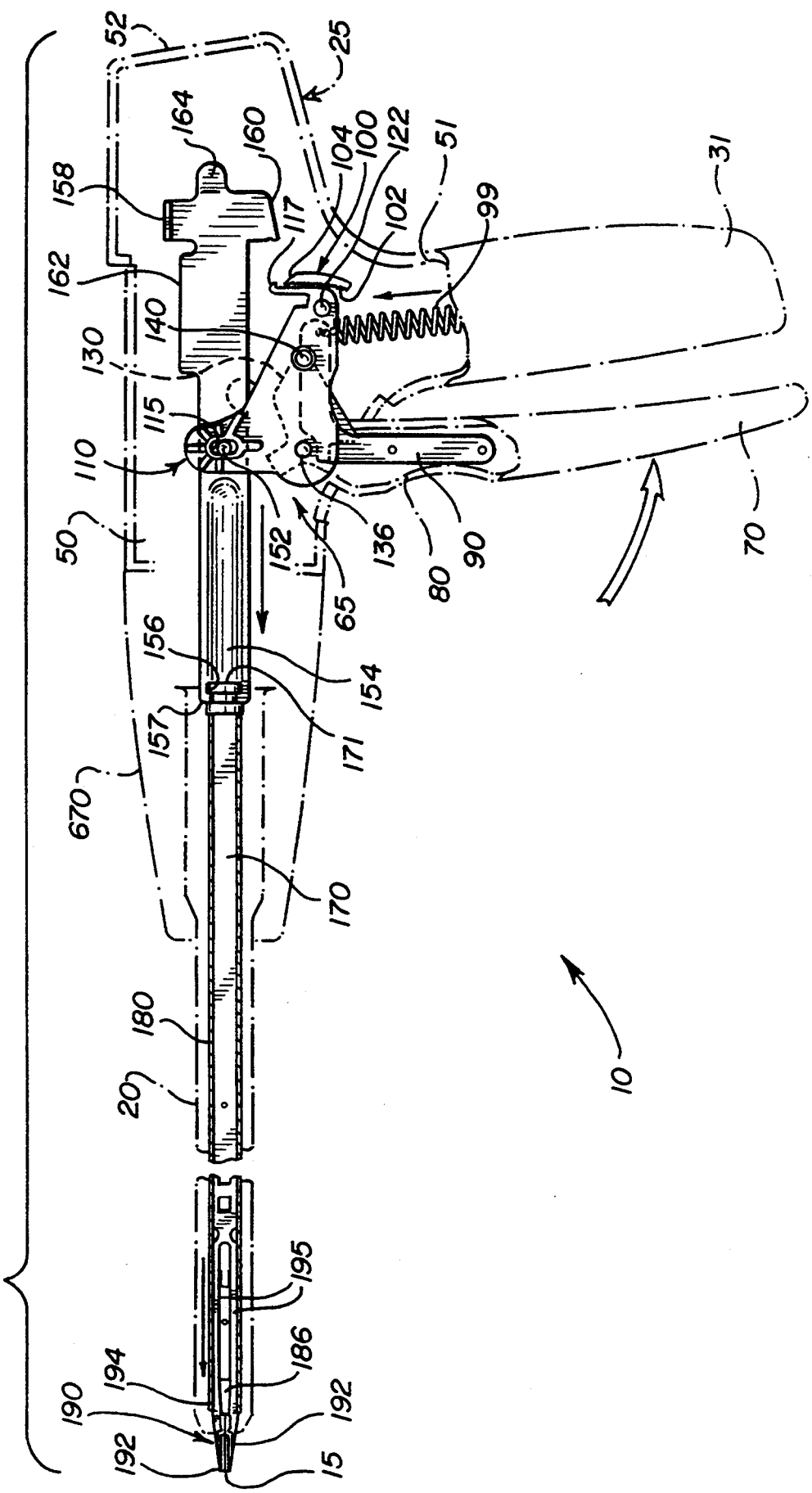
FIG. 16 is a view similar to FIG. 15 showing the actuation of the ligating clip forming system.

As can be seen in FIG. 6, FIG. 15, and FIG. 16, the clip forming elements of the clip applier mechanism 10 of the present invention include the former plate assembly 150, the compression coupling 170, the cam channel 180, and the jaw assembly 190. The former plate assembly 150 is seen to be an elongate plate member having a distal coined groove 154 and a distal slot 156. The coined groove 154 provides clearance for the feed rod 310 as it is pulled back proximally by the feed plate 260. Adjacent to the distal slot 156 is the coined member 157. The coined member 157 and the slot 156 form part of the rotational means for cam channel 180. The former plate assembly 150 is slidably mounted, longitudinally, in housing 39 of left frame 30 between feed plate 260 and extension plate 540. As used herein, longitudinally is defined to mean along the major axis defined by the shaft, while laterally is defined to mean an axis perpendicular thereto extending from left to right. Extending outwardly from the left side of the former plate assembly 150 is a PEM stud 152. Extending upwardly from the proximal end of former plate assembly 150 is the timing wall 158. The timing wall 158 is a tab member which also curves inwardly toward the left frame 30. Extending downwardly from the proximal end of former plate assembly 150 is the lock tab 160 which forms part of the last clip lock-out mechanism. Extending proximally from the proximal end of the former plate assembly 150 is the lead-in tab 164. The lead-in tab 164 prevents binding of return spring 305 between the former plate assembly 150 and feed plate 260. Adjacent to the timing wall 158 is stop tab 162 which extends upwardly and which engages the safety dingus 520 when button 400 is displaced downwardly. The PEM stud 152 is engaged by the drive slot 115 of the former link 110. As previously mentioned, the former plate assembly 150 is slidably mounted, longitudinally, in the left handle 30.

Figure 7:
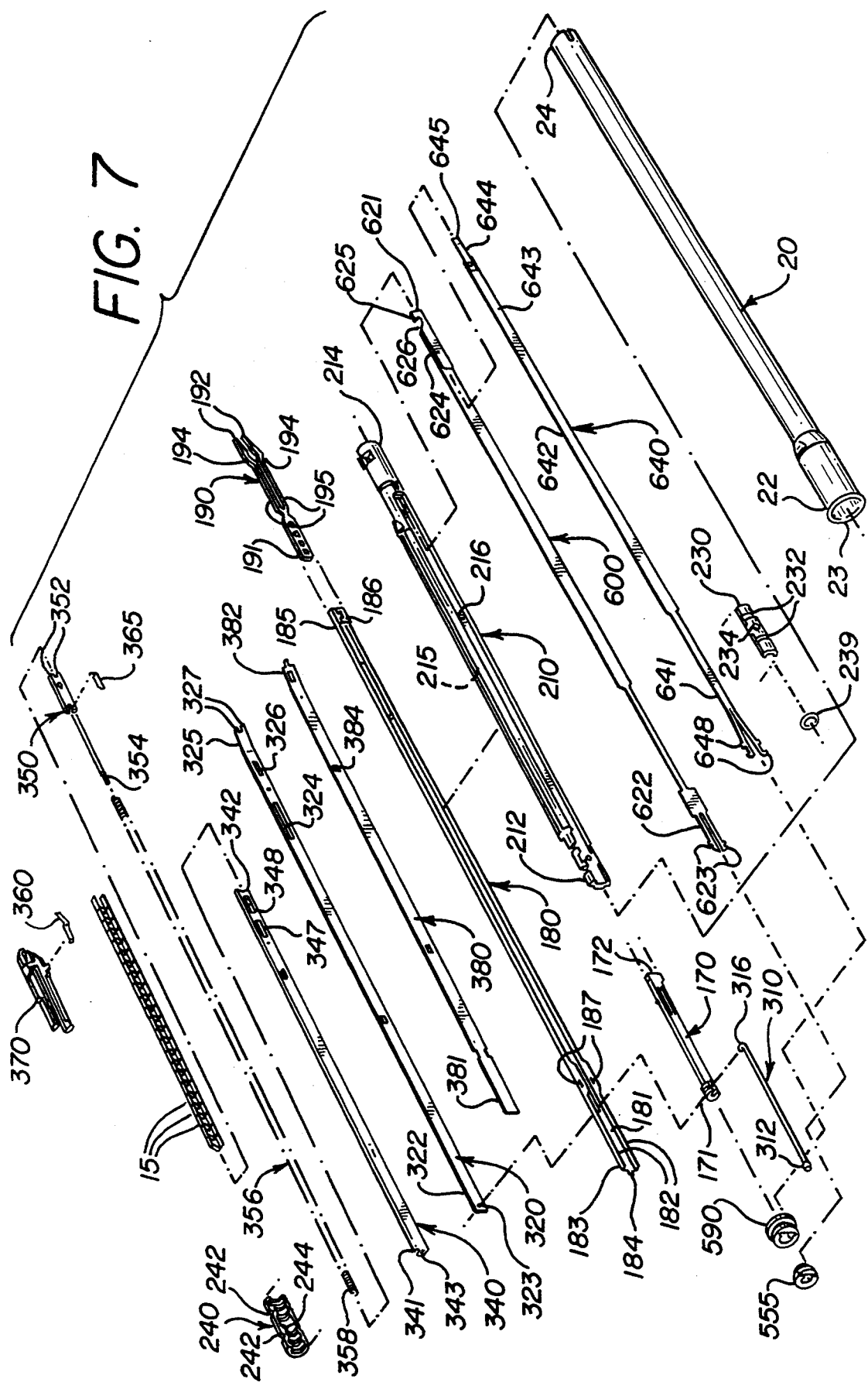
FIG. 7 is a further exploded perspective view of the support tube and related parts comprising the ligation and cutting mechanisms.

Referring to FIG. 6 and FIG. 7, the apparatus 10 of the present invention is seen to have support tube 20 having proximal end 22 and distal end 24. The proximal end 22 of support tube 20 is mounted to the frame 25 through distal apertures 36 and 56. The flange 23 is seen to extend outwardly from proximal end 22 of support tube 20. The proximal end 22 of support tube 20 is free to rotate within the distal end of frame 25. The proximal end 22 of support tube 20 is restrained longitudinally from distal movement within frame 25 by shoulders 40 within left frame 30 and right frame 50 which can act upon flange 23. It can be seen that flange 23 is positioned behind shoulders 40 and in front of backward retention pins 42 contained in left frame 30 and right frame 50 to allow rotation of tubular member 20 while preventing longitudinal movement of tubular member 20 both proximally and distally.

Referring to FIG. 7, FIG. 9, FIG. 15 and FIG. 16, the endoscopic ligation and division apparatus 10 is also seen to have jaw member assembly 190 mounted to the distal end of lower shroud 210. Jaw member assembly 190 is an elongate member consisting of a proximal mounting member 191 and distal elongate jaw members 192 extending from elongate beam members 195. Elongate jaw members 192 have retention grooves 193 for receiving ligating clips 15. Jaw members 192 are angulated with respect to each other as well as being moveable toward each other when beam members 195 are deflected inwardly. The jaw members 192 are seen to have exterior cam surfaces 194 for interacting with cam channel 180 to close the members 192 about a ligating clip 15. Cam channel 180 is an elongate channel member, slidably mounted, longitudinally, in the lower shroud 210. Cam channel 180 has a web 181 and perpendicular flange members 182 extending therefrom.

Mounted to the distal end 185 of cam channel 180 is a hollow, rectangular box-like structure 186 which engages jaw member assembly 190 and is slidable, longitudinally, about the jaw member assembly 190. The structure 186 interacts with the cam surfaces 194 to close the jaw members 192 about a ligating clip 15 by causing beam members 195 to deflect inwardly. The proximal end 183 of cam channel 180 contains mounting slots 187 for receiving mounting posts 175 of compression coupling 170. Also located in the proximal end 183 of cam channel 180 is the locating tab 184.

As can be seen in FIG. 6, FIG. 7, FIG. 15 and FIG. 16, compression coupling 170 is an elongate member linking cam channel 180 with former plate assembly 150. The proximal end 171 of compression coupling 170 is rotatably engaged by distal slot 156 and coined member 157 of former plate assembly 150, allowing cam channel 180 to rotate with respect to the former plate assembly 150. The distal end 172 of compression coupling 170 fits within and engages cam channel 180 via mounting posts 175 and return tabs 174. Return tabs 174 of compression coupling 170 engage distal edges of flange members 182 of cam channel 180. Compression coupling 170 has mounting posts 175 for engaging slots 187 in cam channel 180, and cavity 176 for receiving locating tab 184 of cam channel 180. Locating tab 184 aligns the mounting posts 175 and slots 187. Compression coupling 170 also has longitudinal slot 177 through which feed rod 310 is slidably mounted, longitudinally, in a concentric configuration.

As can be seen in FIG. 7, the lower shroud 210 is an elongate member having proximal end 212 and distal end 214. The lower shroud 210 is mounted within tubular member 20. The lower shroud 210 has a first longitudinal passage 215 for mounting cam channel 180, floor 380, feed bar 320 and clip track 340. Shroud 210 also has a lower, second longitudinal passage 216 for mounting blade assembly 640 and J-hook 600.

Referring to FIGS. 13-19, rotating the trigger assembly 65 about pivot journals 37 and 57 causes driving rib 86 of right trigger 80 to engage face 138 of clutch 130, therefore rotating clutch 130 with trigger assembly 65. Clutch engagement pin 140, which is contained within the engagement hole 124 of former link 100 during clip forming, causes the former link 110 to rotate about the axis defined by pivot axle 135. As best seen in FIG. 15, the PEM stud 152 of the former plate assembly 150 is engaged within the drive slot 115 of former link 110 causing the former plate assembly 150 to displace distally, longitudinally, along the longitudinal axis of the apparatus 10 as the former link 110 rotates with the trigger assembly 65 about the pivot journals 37 and 57. Distal displacement of the former plate assembly 150 causes the compression coupling 170 to displace cam channel 180 distally in a longitudinal direction. This causes the rectangular, box-like structure 186 mounted to the distal end 185 of cam channel 180 to slide over the jaw member assembly 190, thereby engaging the cam surfaces 194. This causes the jaw members 192 (and the beam members 195) to displace inwardly about a clip 15 to close or form the clip 15. The cam channel 180 is able to rotate with respect to the former plate assembly 150 because of the compression coupling 170. The proximal end 171 of the compression coupling 170 is rotatably engaged by the slot 156 and the coined member 157 of the former plate assembly 150. The distal end 172 of compression coupling 170 is snapped into the proximal end 183 of cam channel 180 between the flanges 182 and web 181. In addition, the mounting posts 175 of compression coupling 170 are engaged by a snap fit in retention slots 187 contained in cam channel 180.

Figure 13:
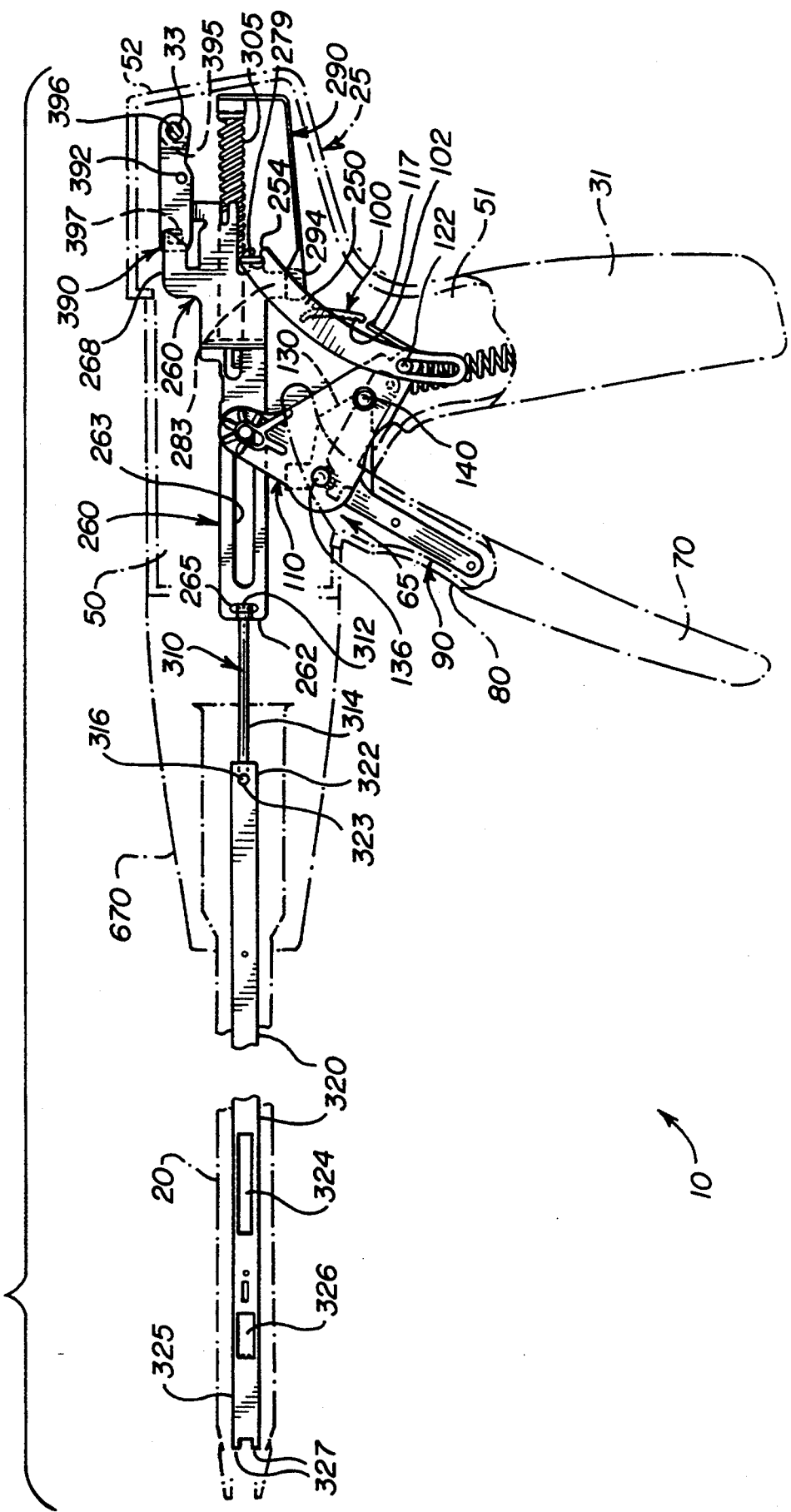
FIG. 13 is a side elevational view of the apparatus showing the ligating clip feeding system at rest wherein certain parts have been omitted for clarity.
Figure 14:
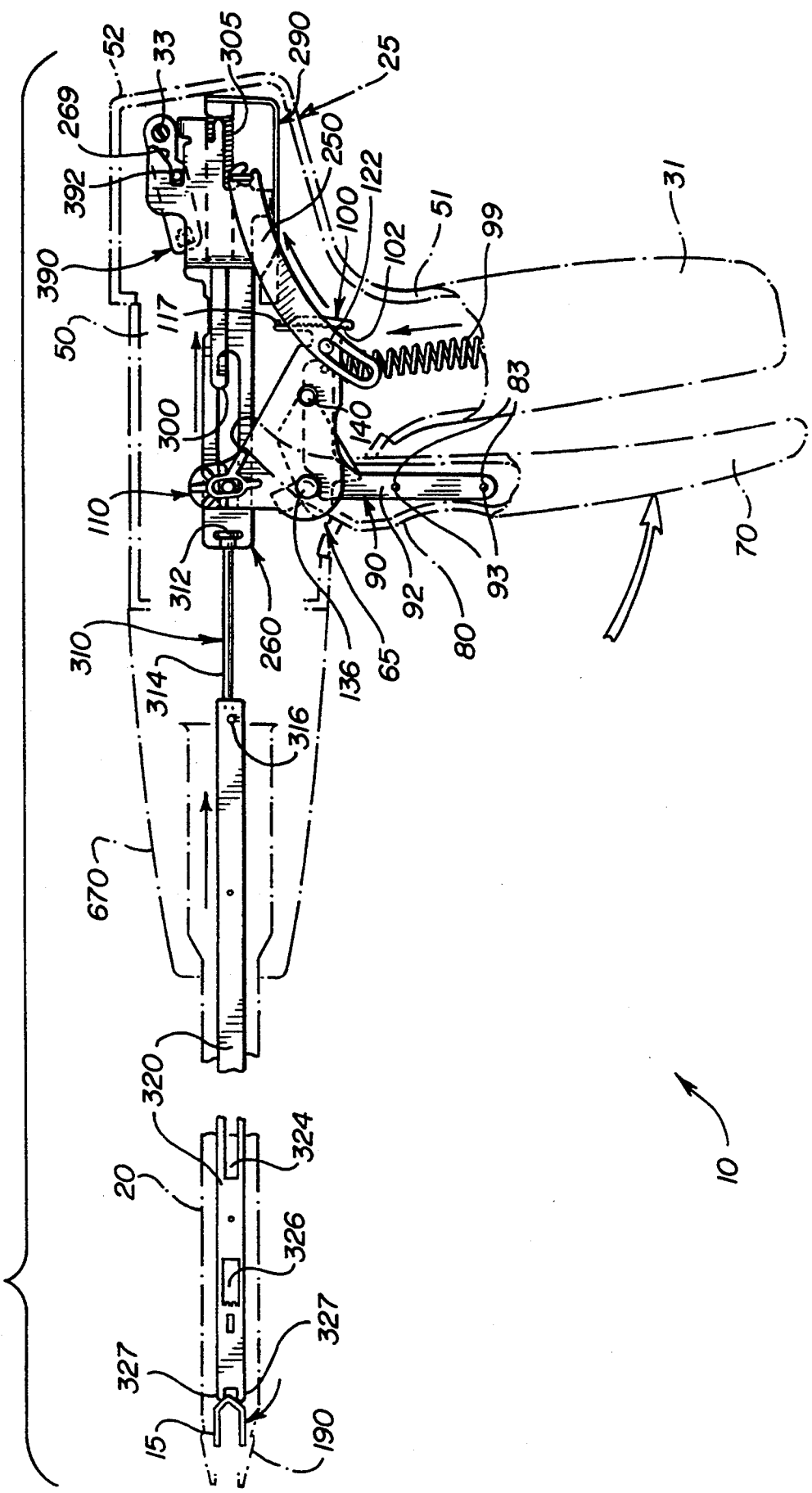
FIG. 14 is a view similar to FIG. 13 showing the actuation of the ligating clip feeding system.

Referring to FIG. 6, FIG. 13 and FIG. 14, the clip feeding elements of the apparatus 10 of the present invention include the feed link 250, the feed plate 260, the feed rod 310, the clip track 340, the feed bar 320, the floor 380, the feed shoe 350, feeder spring 356, lock lever 365, lifter spring 360, precock trigger 390, spring guide 290 and return spring 305. The feed plate 260 is slidably mounted, longitudinally, in the housing 39 of left frame 30 between the former plate assembly 150 and the inner wall of the left frame 30. Feed plate 260 is an elongate plate having a distal end 262 and an offset proximal end 264. Extending from the top of proximal end 264, is the precock cam 268. The precock cam 268 has proximal cam surface 269. It can be seen that slot 267 separates the precock cam 268 from the proximal end 264 of the feed plate 260. Extending downwardly from the bottom of proximal end 264, and curving toward right frame 50, is the last clip lockout tab 283. Last clip lockout tab 283 interacts with tab member 294 of the spring guide 290. Extending proximally, and toward left handle 30, from the bottom of proximal end 264 is the feed tab 279. The feed tab 279 is engaged by the feed link 250. Extending from the top of proximal end 264, upwardly and toward right handle 50, is the precock return tab 274. The precock return tab 274 interacts with precock trigger 390. The feed plate 260 has clearance slot 263 in which PEM stud 152 of former plate assembly 150 is free to travel. The feed plate 260 also has feed rod slot 265 at its distal end 262 for receiving and rotatably engaging the head 312 of the feed rod 310. The feed rod 310 is an elongate member having a shaft 314 and also having a cylindrical head 312 at its proximal end and a hook 316 at its distal end.

It can be seen that the feed link 250 is a curved, elongate member having a slot 252 in its lower end and having at its upper end a c-shaped portion 254. The c-shaped portion 254 of the feed link 250 pivotally engages the feed plate 260 at the feed tab 279. Drive pin 122 extending from drive link 120 of former link 110 is free to travel within the clearance slot 252 of the feed link 250.

The feed bar 320 is an elongate plate-like member which is slidably mounted, longitudinally, in lower shroud 210. The feed bar 320 has distal end 325 and proximal end 322 containing hole 323. Hole 323 receives the hook 316 of the feed rod 310. The feed bar 320 is seen to have a pair of distal elongate tips 327 for displacing clips 15 from the clip track 340 to within the retention grooves 193 of the jaw member assembly 190. The feed bar 320 also has a rectangularly-shaped displacement slot 324 and the primary valve slot 326 located toward its distal end. The clip track 340 is seen to be an elongated channel-shaped member for receiving and retaining a plurality of clips 15. The clip track 340 is mounted in the lower shroud 210. The clip track 340 has proximal end 341 and distal end 342. A feeder spring 356 acting on a feed shoe 350 provides a distal biasing force against the clips 15. Located toward the distal end 342 of clip track 340 are lock lever slot 347 and primary valve 348.

Figure 8:
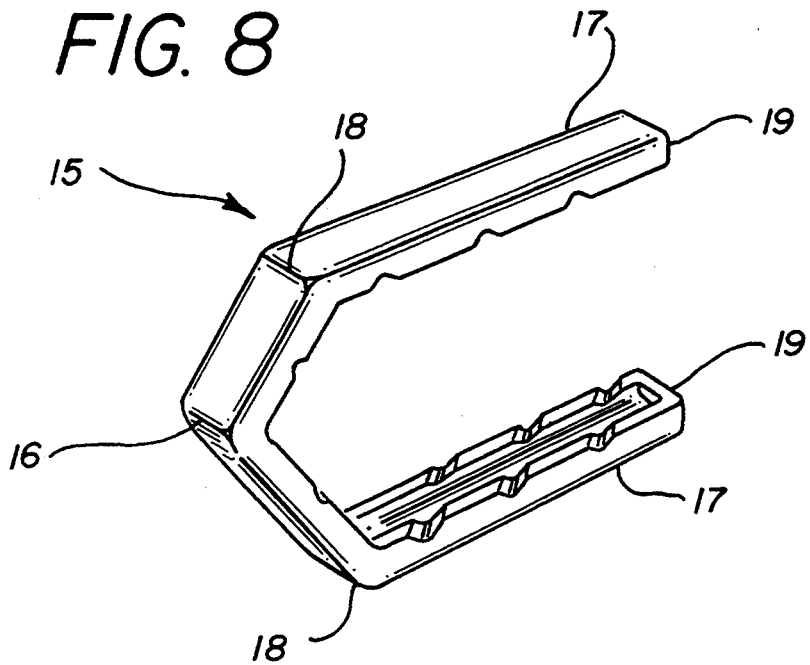
FIG. 8 is a perspective view of a ligating clip.
Figure 9:
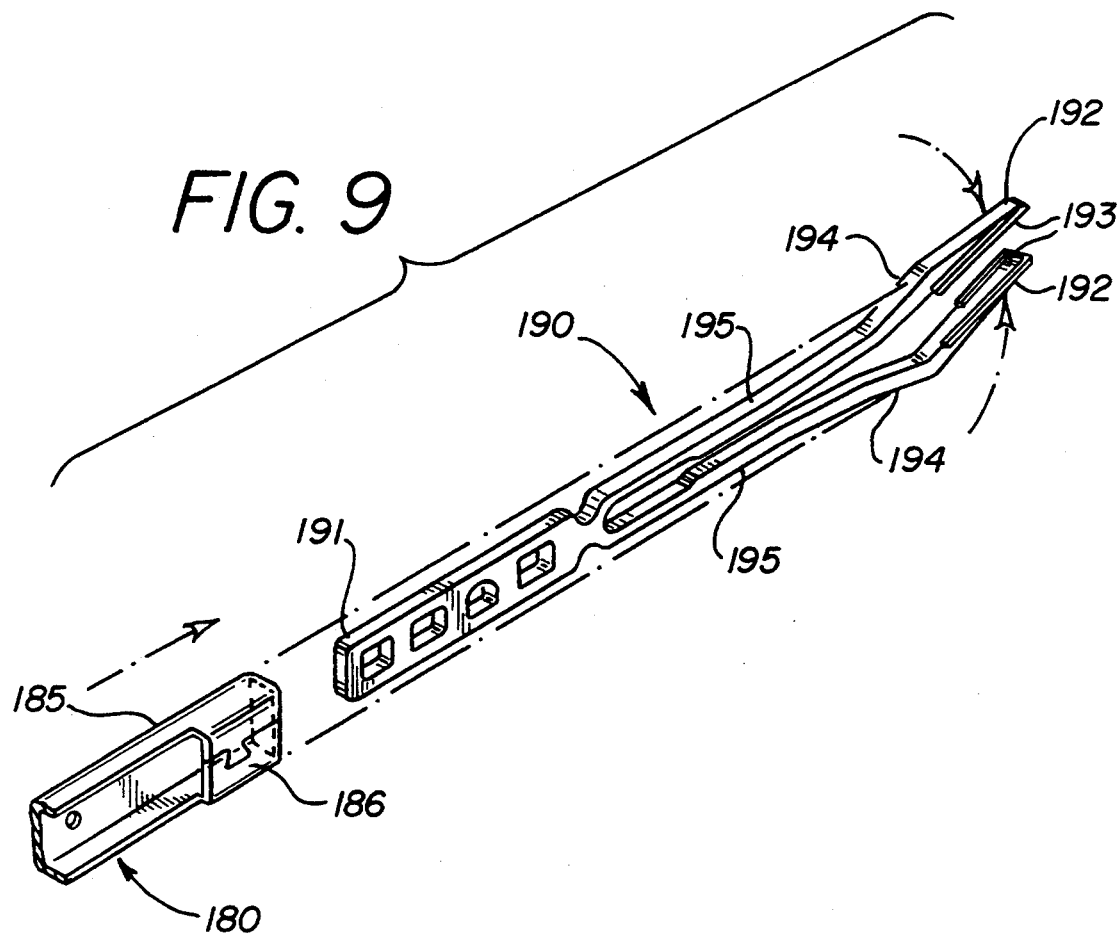
FIG. 9 is an exploded view of the cam channel and jaw assembly used to form a ligating clip.

As seen in FIG. 8, the clips 15 are typical, conventional ligating clips used in this art and equivalents thereof. The clips 15 are seen to have an apex 16 and legs 17. The legs 17 are seen to extend angularly outward from the apex 16 to the knees 18 where the legs 17 are seen to change direction and bend inwardly and extend substantially parallel to the longitudinal axis of the clips 15 to distal ends 19 of the legs 17. The clips 15 are loaded into the clip track 340 in a head-to-toe configuration. That is, the apex 16 of each clip 15, is proximal to the legs 17. The distal ends 19 of each clip 15 touch the knees 18 of a distal clip 15.

Referring to FIG. 6, FIG. 7, FIG. 13 and FIG. 14, feed shoe 350 is slidably mounted, longitudinally, in clip track 340 and forces the clips 15 forward along the clip track 340 for feeding into the jaw member assembly 190. Feed shoe 350 is seen to have distal prongs 352 (for engaging a clip 15) and proximal spring guide shaft 354 on which feeder spring 356 is concentrically mounted. Feeder spring 356 provides a distal biasing force against feed shoe 350. The proximal end 358 of feed spring 356 abuts proximal folds 343 located in the proximal end 341 of clip track 340. The floor 380 is an elongate plate like member having tabs 384, proximal end 381 and distal end 382. The floor 380 is mounted in the lower shroud 210. The tabs 384 of the floor 380 fit into and are engaged by the displacement slot 324 of feed bar 320. The lock lever 365 is an "L" shaped part mounted to the distal end of the feed shoe 350 and functions as part of the last clip lockout mechanism. After the last clip 15 remaining in the clip track 340 is fed into the jaw member assembly 190, the short leg of "L" shaped lock lever 365 contacts top shroud 370, forcing the long leg of the "L" shaped lock lever 365 to rotate through the lock lever slot 347 in the clip track 340 and through the primary valve slot 326 in the feed bar 320, thereby blocking the feed bar 320 from completely returning. The lifter spring 360 is mounted to the top shroud 370 and functions to translate a clip 15 from the level of the clip track 340 to the level of the feed bar 320.

The feed mechanism of the apparatus 10 operates in the following manner. As the trigger assembly 65 is rotated in a clockwise position within journals 37 and 57, feed link 250 pivots in a counter-clockwise direction about feed tab 279. The feed link 250 is driven by drive pin 122 of former link 110 acting on slot 252 of feed link 250. C-shaped portion 254 of feed link 250, which engages the feed plate 260 at feed tab 279, displaces the feed plate 260 in a proximal direction and compresses return spring 305. This proximal displacement of feed plate 260 causes the feed rod 310 and the feed bar 320 to be displaced proximally. When feed bar 320 is initially displaced proximally, primary valve 348 of clip track 340 is closed to prevent more than one clip 15 from being staged onto the lifter spring 360. During continued proximal travel of feed bar 320, distal end 325 clears lifter spring 360 allowing lifter spring 360 to translate staged clip 15 onto distal end 382 of floor 380 at the level of feed bar 320. When the trigger assembly 65 is released, it is caused to rotate in a counterclockwise direction, because of the biasing force of the trigger spring 99. The precock trigger 390 releases the feed plate 260 allowing the distal bias of return spring 305 to displace feed plate 260 and feed rod 310 distally causing the feed bar 320 to be displaced distally. The distal tips 327 of feed bar 320 engage the positioned clip 15 and push the clip 15 into the retaining grooves 193 of the jaw member assembly 190 as the feed bar 320 returns to its atrest position. Also during distal displacement of feed bar 320, the distal end 325 of feed bar 320 deflects lifter spring 360, preloading it, in preparation for next clip 15. When feed bar 320 nears completion of its distal displacement, primary valve slot 326 clears primary valve 348 of clip track 340. This opens primary valve 348 allowing the next clip 15 within clip track 340 to be staged onto lifter spring 360. The feed bar 320 is rotational with respect to feed plate 260 since the head 312 of feed rod 310 is rotatably engaged in feed rod slot 265.

Referring to FIG. 5, FIG. 6, FIG. 13 and FIG. 14, the spring guide 290 is a spring member having a base 291 containing longitudinal locking slot 296. The spring guide 290 also has longitudinal spring member 298 extending from its proximal end. The spring member 298 has distal hook 300. Return spring 305 is concentrically mounted onto spring member 298. The spring guide 290 is mounted to left frame 30 and functions to prevent the jaw 190 from being actuated after the last clip 15 contained in clip track 340 is fired. It performs this function in the following manner. The lock tab 160 of former plate assembly 150 is positioned within the locking slot 296 of the spring guide 290. The last clip lockout tab 283 of feed plate 260 is positioned on top of cam member 294 causing the base 291 to displace sufficiently downward so that the locking tab 160 is no longer within the locking slot 296. The former plate assembly 150 is then free to displace distally to form a clip 15. As the former plate assembly 150 slides distally during actuation, the feed plate 260 slides proximally. As the feed plate 260 slides proximally, the last clip lockout tab 283 of the feed plate 260 disengages the cam member 294 extending from the distal end of the base 291 of the spring guide 290 causing the base 291 to displace upward. After the last clip is fired from the clip track 340, the lock lever 365 rotates through the slot 326 on the feed bar 320 preventing the feed bar 320 from completely displacing distally. Since feed bar 320 cannot displace distally, last clip lockout tab 283 is not available to act against cam member 294. Consequently, lock tab 160 is contained within the locking slot 296 of spring guide 290 preventing the former plate assembly 150 from moving forward. Since the former plate assembly 150 cannot be displaced distally, cam channel 180 cannot be displaced distally to actuate jaw members 192. Consequently, it is not possible to actuate jaw members 192 after the last clip 15 has been fired.

As seen in FIG. 5, FIG. 13 and FIG. 14, the precock trigger 390 is an elongate member having proximal bushing end 395 with hole 396 therethrough. The precock trigger 390 also has pin 392 extending outwardly from the central, left hand side of the precock trigger 390. The precock trigger 390 also has timing latch 397 extending outwardly from its right hand side along the distal end. The precock trigger 390 is pivotally mounted in left frame 30 on precock trigger pivot pin 33 which is engaged in hole 396 of the bushing 395. The precock trigger 390 is responsible for timing the feeding of a clip 15 into the jaw member assembly 190 in the following manner. As the feed plate 260 is displaced proximally by the feed link 250 in response to actuation of the trigger assembly 65, the pin 392 on precock trigger 390 rides along the cam surface 269 on the precock cam 268 and is contained in the slot 267 located between the bottom of precock cam 268 and the top of the proximal end 264 of feed plate 260. This causes clockwise rotation of the precock trigger 390 about pin 33. The ramp surface 398 on the timing latch 397 flexes the precock trigger 390 around the timing wall 158 of former plate assembly 150 as the precock trigger is rotated during the initial stroke. After the forming stroke is completed, trigger assembly 65 is typically released by the surgeon. The bias provided by the trigger spring 99 acting upon the trigger assembly 65 causes the assembly 65 to rotate in a counter-clockwise direction. On the trigger return stroke, the precock return tab 274 engages a cam surface on the precock trigger 390 trying to rotate the precock trigger 390 counter-clockwise about pin 33. The precock trigger 390 cannot be rotated until the timing latch 397 is no longer engaged by the timing wall 158. Therefore, feed plate 260 cannot move forward until precock trigger 390 is rotated. Precock trigger 390 is not released by timing wall 158 of former plate assembly 150 until ligating mechanism returns sufficiently to allow jaw member assembly 190 to open completely. Once timing latch 397 is no longer engaged by timing wall 158, the bias force of return spring 305 causes feeder plate 260 to displace in a distal direction and feed a clip 15 to the jaw member assembly 190 as discussed above.

As can be seen in FIG. 1, FIG. 5, FIG. 17, FIG. 18 and FIG. 19, the cutting mechanism of the apparatus 10 of the present invention consists of a knife extension mechanism and a knife cutting mechanism. The knife extension mechanism comprises a number of elements including the extension plate 540, button 400, button spring 500, base 510, safety dingus 520, snap rod 530, extension coupling 555, and J-hook 600. When the cutting mechanism is engaged, the forming and feeding mechanisms are deactivated by clutch 130 and safety dingus 520.

The button 400 is seen to have downwardly extending snap rod post 405 and downwardly extending tab members 407. The button 400 has upwardly extending top surface portion 402 for grasping and pushing. Button spring 500 is concentrically mounted about snap rod post 405. Button 400 and button spring 500 are mounted to base 510. Base 510 is seen to be mounted in aperture 58 of the frame 25. The base 510 has aperture 512 for receiving snap rod post 405 and tab mounting holes 514 for receiving tabs 407. The button spring 500 provides an upward bias against the button 400. The base 510 has base snaps 515 extending downwardly into the aperture 58 and into the cavity of the handle 25. The base snaps 515 engage base prongs 546 of extension plate 540. Extending downward from the button 400 between the base prongs 546 is the snap rod 530. The snap rod 530 is an elongate member having at its lower end a pin 532 extending therefrom. The upper end 534 of the snap rod 530 fits into and is engaged by the snap rod post 405. The safety dingus 520 is seen to have a lower member 524 and an upper C-shaped end section 522. The safety dingus 520 is slidably mounted in left frame 30 perpendicular to the longitudinal axis of the apparatus 10. The C-shaped section 522 of safety dingus 520 engages pin 532 of snap rod 530. The safety dingus 520 functions in the following manner. When the button 400 is pushed downward, the safety dingus 520 also moves downward in a simultaneous fashion. The proximal end of C-shaped section 522 engages the distal end of the tab 162 of former plate assembly 150, thereby preventing the former plate assembly 150 from displacing distally. The ligation mechanism is therefore locked out immediately because the former plate assembly 150 cannot displace distally and form a clip 15.

The extension plate 540 is an elongate plate-like member, slidably mounted, longitudinally, in housing portion 59 of right frame 50 having base prongs 546 for engaging base snaps 515. The extension plate 540 has cam tabs 542 and 544 for engaging cam member 142 of clutch 130. Slot 548 is contained within extension plate 540 and provides clearance for coined groove 154 and coined member 157 of former plate assembly 150. At the distal end of extension plate 540 is coined member 550 and extension coupling slot 552. The extension coupling 555 fits within and is rotatably engaged by extension coupling slot 552 and coined member 550.

Referring now to FIG. 3, FIG. 4, FIG. 7, FIG. 10, FIG. 11 and FIG. 12, it can be seen that the J-hook 600 is a plate-like member having proximal end 622 and isolation hook 625 at distal end 621. The isolation hook 625 is formed by folding a piece of the distal end 621 of J-hook 600 over and onto itself thereby forming a channel 624 for receiving the blade assembly 640. The hook shaped openings 626 are preferably cut out, using conventional metal cutting means such as die cutting, lasers and the like, prior to folding the distal end 621. However, the hook-shaped openings 626 can also be cut out after the distal end 621 has been folded to form channel 624. The proximal end 622 of the J-hook 600 has prongs 623 for engagement with extension coupling 555.

The cutting assembly includes blade assembly 640, mid link 560, plunger link 570, plunger plate 580, and plunger coupling 590. The blade assembly 640 consists of a slidably mounted, longitudinally, carrier 642 and a blade 644. The carrier 642 is an elongate member to which the blade 644 is attached. The blade 644 is affixed to the distal end 643 of carrier 642 by conventional methods such as spot welding. The blade 644 is manufactured from conventional cutting blade materials such as conventional stainless steels. The blade edge 645 is manufactured using conventional manufacturing methods such as grinding. The proximal end 641 of the blade assembly 640 has a pair of proximally extending prongs 648 which are engaged by plunger coupling 590. The blade assembly 640 is slidably contained within channel 624 of isolation hook 625. The J-hook 600 and the blade assembly 640 are slidably mounted, longitudinally, in the lower channel 216 of the lower shroud 210.

Figure 17:
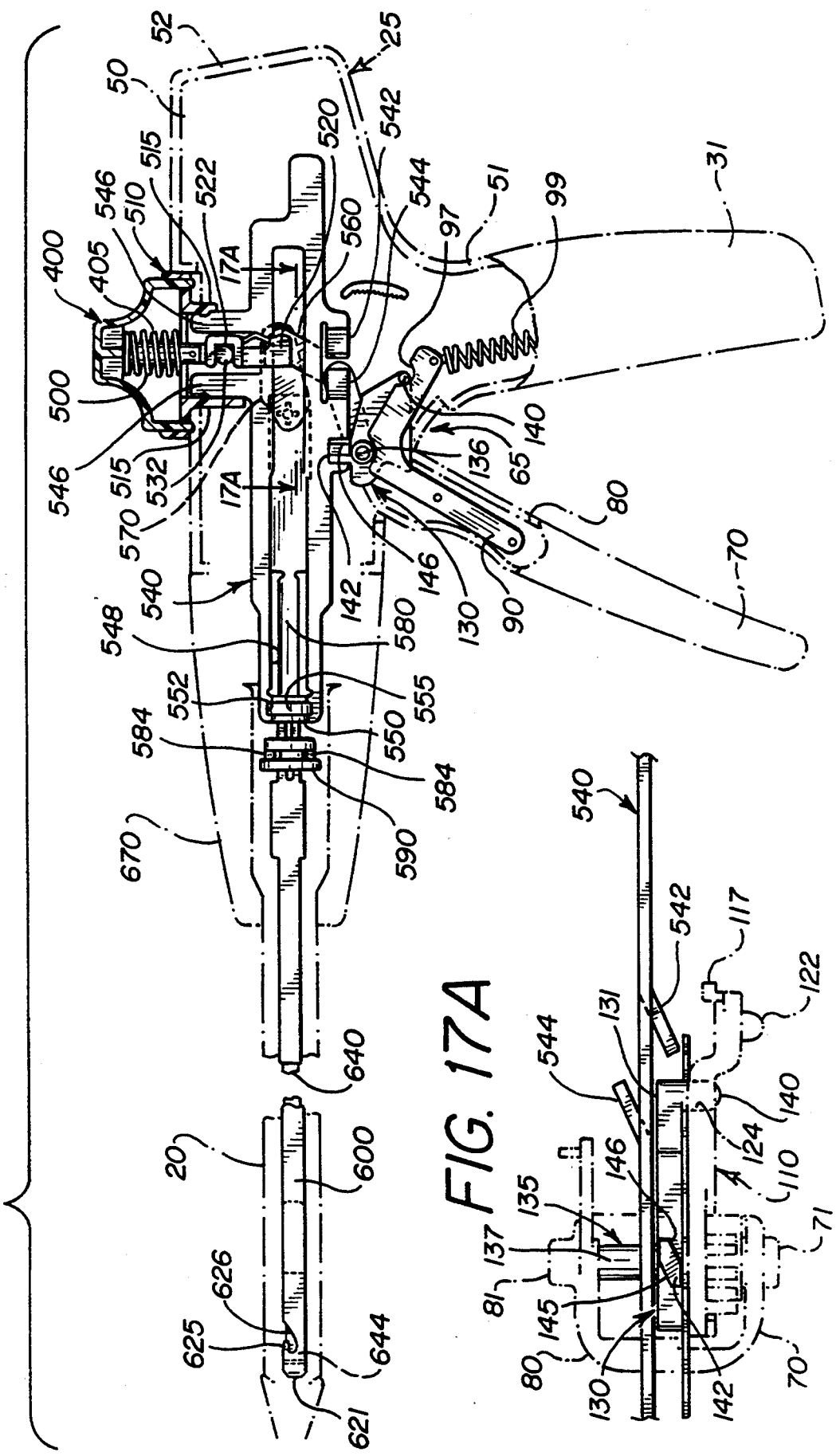
FIG. 17 is a side elevational view of the apparatus showing the cutting means at rest wherein certain parts have been omitted for clarity.
Figure 18:
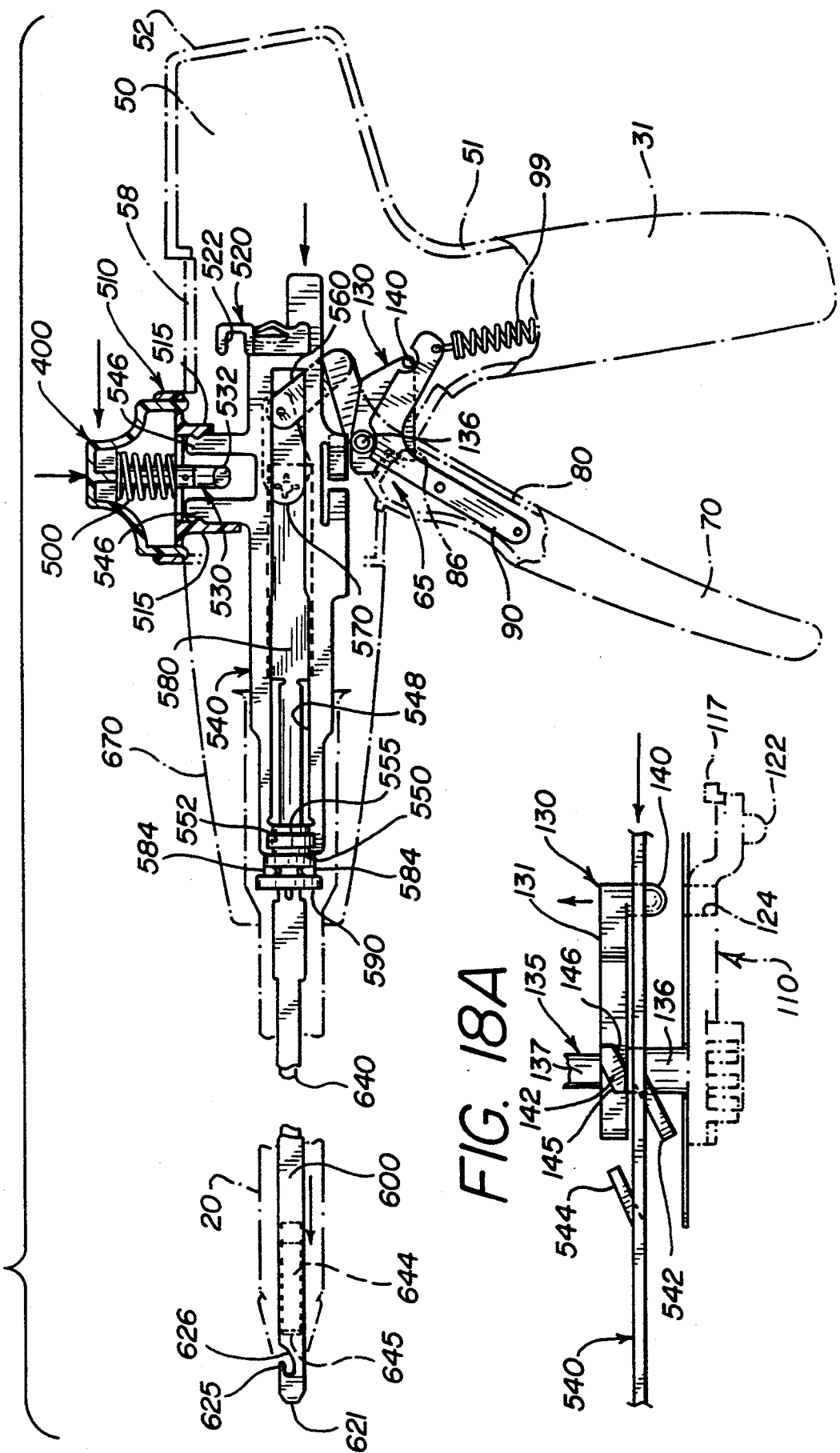
FIG. 18 is a view similar to FIG. 17 showing the cutting blade and related parts at rest after extension.
Figure 19:
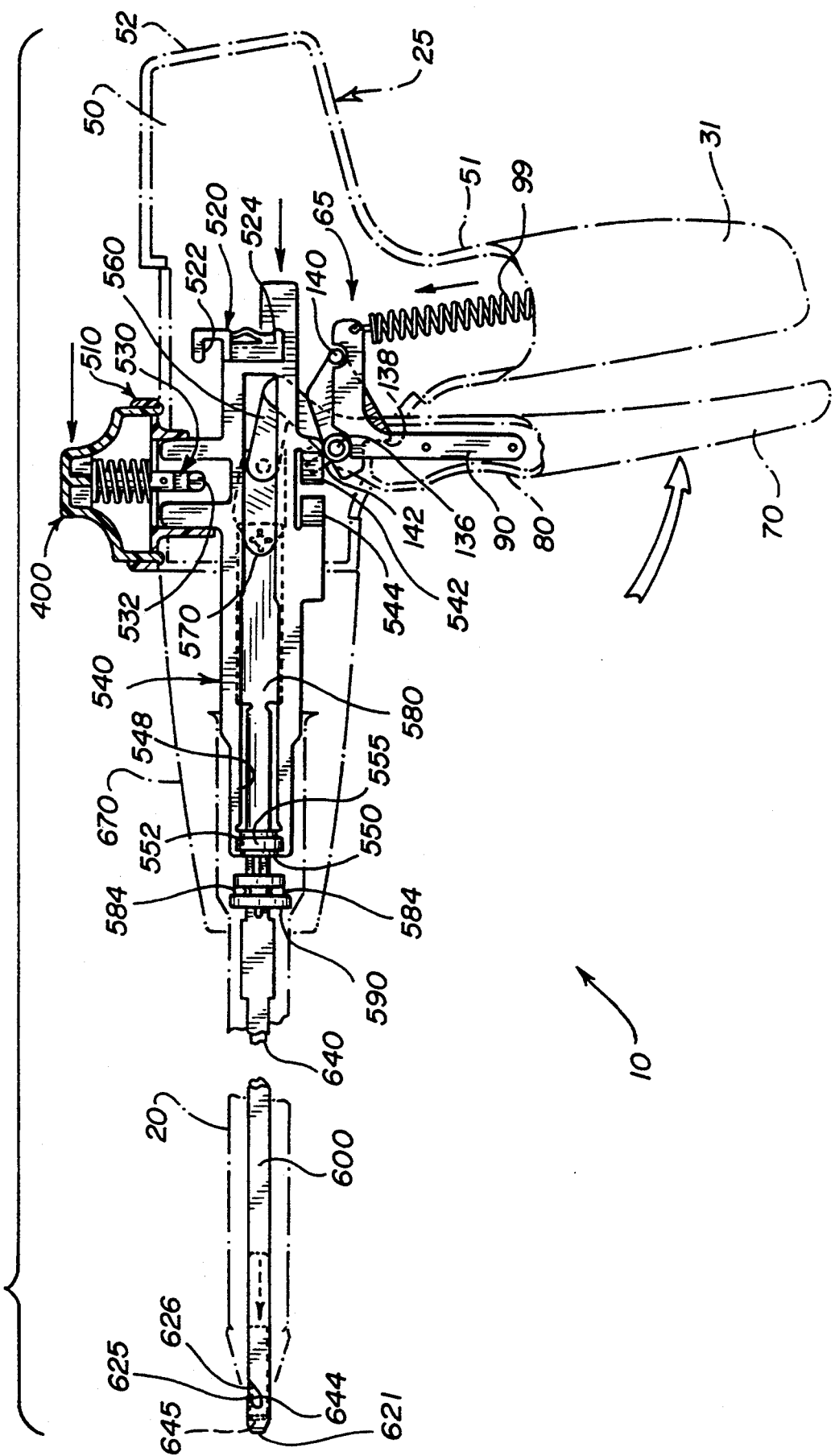
FIG. 19 is a view similar to FIG. 18 showing the actuation of the cutting means.

As can be seen in FIGS. 17-19, the cutting mechanism is actuated, and the apparatus 10 is switched from a ligating mode to a cutting mode, in the following manner. When the button 400 is displaced downwardly against spring 500, the safety dingus 520 and snap rod 530 are displaced downwardly. C-section 522 of safety dingus 520 engages the distal side of stop tab 162 of former plate assembly 150. During distal displacement of button 400 and base 510, pin 532 of snap rod 530 interacts against track rib 41 of left handle 30, preventing the spring bias force of button spring 500 from returning button 400 to its upward position. As the base 510 and button 400 are displaced distally in slot 58, the extension plate 540 is caused to displace distally and the cam tab 542, extending from the bottom of the extension plate 540, is made to contact the disengagement cam surface 146 of the cam member 142 on the clutch 130. This displaces the clutch 130 laterally to the right causing the engagement pin 140 of clutch 130 to displace out from the engagement hole 124 of the former link 110. Consequently, former and feeding mechanisms are completely disengaged since the former link 110 is, resultingly, no longer engaged by the trigger assembly 65. Simultaneously, the isolation hook 625 of the J-hook 600 is fully extended distally out from lower shroud 210, beyond jaw member assembly 190, to the cutting position, due to J-hook 600 connection to extension plate 540 through extension coupling 555. At this time pin 532 of snap rod 530 clears track rib 44 of left handle 30 allowing the bias force of button spring 500 to displace button 400 and snap rod 530 vertically. Proximal displacement of J-hook 600, extension coupling 555, extension plate 540, base 510 and button 400 is prevented due to pin 532 of snap rod 530 engagement of retention wall 45 of left handle 30.

Referring to FIG. 6, and FIGS. 17–19, the mid link 560 is seen to have pivot holes 562 on either end. The midlink 560 is pivotally mounted on one end thorough pivot hole 562 to trigger link 85 extending from right trigger 80 by pin 87. The other end of mid link 560 is pivotally mounted to proximal pin 572 extending from the proximal end of plunger link 570. Plunger link 570 has proximal pin 572 and distal pin 574. The plunger plate 580 is seen to have proximal opening 582 and distal ends 584, each bent at a 90 degree angle from the longitudinal axis of the plunger plate 580. The distal pin 574 of the plunger link 570 is pivotally connected to plunger plate 580 through pivot hole 582. The proximal pin 572 rides in the cutting track groove 53 contained in the inner wall of right frame 50. The ends 584 of plunger plate 580 are rotatably engaged within groove 591 of plunger coupling 590. The split end members 648 of blade assembly 640 are also engaged by plunger coupling 590, thereby permitting rotation of blade assembly 640. During extension of the cutting mechanism, the extension coupling 555 is made to contact plunger coupling 590 causing distal displacement of blade assembly 640, plunger plate 580, plunger link 570, and mid link 560. The distal pin 572 of plunger link 570 is positioned into the cutting track groove 53 of right handle 50 due to the displacement of above components, hence the cutting mechanism is enabled.

Referring to FIG. 19, when the trigger assembly 65 is rotated in a clockwise fashion about pivot journals 37 and 57, plunger plate 580 is caused to be displaced distally along the longitudinal axis of the apparatus 10 by trigger link 85, mid link 560 plunger link 570 and cutting track groove 53. The cutting track groove 53 confines pin 572 plunger link 570 to translate only in a longitudinal direction. This causes plunger coupling 590 and blade assembly 640 to be similarly displaced, therefore moving the blade 644 within channel 624 and through the hooked shaped opening 626 of isolation hook 625. Release of trigger assembly 65 similarly causes the blade to be retracted in a proximal direction to its resting position due to the bias force of trigger spring 99.

Referring now to FIG. 17A and FIG. 18A, the cutting mechanism is de-activated, and the apparatus 10 is returned or switched to the ligating mode, by pushing down on the button 400 causing pin 532 of snap rod 530 to clear retention wall 45 of left handle 30. Displacing the base 510 and button 400 in a proximal direction thereby displaces the extension plate 540 in a proximal direction. As the extension plate 540 is displaced proximally, the cam tab 544 engages the engagement cam surface 145 of cam member 142 on the clutch 130 thereby causing the engagement pin 140 to laterally slide into and re-engage engagement hole 124, thereby re-engaging the former link 110 to trigger assembly 65. Also, rod member 532 of snap rod 530 is re-engaged in c-shaped member 522 of safety dingus 520. As button 400 is pushed upward by button spring 500, safety dingus 520 is pulled upward by snap rod 530 away from the stop tab 162 of former plate assembly 150. The forming mechanism is now activated and the cutting mechanism is deactivated. Deactivation of the cutting mechanism occurs because the mid link, at its full proximal position, is such that rotation of trigger assembly 65 does not cause longitudinal displacement of the cutting mechanism. As the extension plate 540 displaces proximally, it causes the isolation hook 625 to also displace proximally into the lower shroud 210, such that distal end of isolation hook 625 is proximal to jaw members 192.

As seen in FIG. 5, the knob 670 and the knob ring 680 are mounted over the support tube 20 and onto the frame 25. Rotating the knob 670 will cause the distal end of the apparatus 10, including support tube 20, to rotate. The knob 670 and the knob ring 680 are keyed to the support tube 20.

Endoscopic surgical instrumentation typically requires some sort of gas sealing means to prevent the insufflation gas from escaping. Referring to FIG. 7, bottom seal cap 230 and top seal cap 240 are mounted to the proximal end of the lower shroud 210 and fit together to form a cavity. Bottom seal cap 230 has annular grooves 232 and charging hole 234. Top seal cap 240 has annular grooves 242 and charging hole 244. 0-rings 239 are contained within grooves 232 and 242 to both hold seal caps 230 and 240 together and to provide sealing means between the exterior of the seal caps and the interior of tubular member 20. Conventional sealants having sufficient viscosity effective to create a gas seal, such as silicone grease and the like, are charged into the charging holes 234 and 244 to fill the cavity between seal caps 230 and 240 and surround the members passing through the cavity including the sliding members such as the cam channel 180, the feed bar 320, the J-hook 600 and the blade assembly 640.

The ligation and division apparatus 10 of the present invention will be constructed from materials conventional in this art. The materials include plastics such as polycarbonate, nylon, polyetherimide and nitrile and 300 and 400 series stainless steels. The clips 15 are conventionally made from titanium and the like although conventional absorbable materials may also be used. The instrument is typically sterilized after packaging and prior to use using conventional sterilization techniques. It is particularly preferred to sterilize the instrument using cobalt-60 generated radiation.

The endoscopic ligation and division apparatus 10 may be used in conventional endoscopic techniques including cholecystectomy, appendectomy, anastomosis, hernia repair and the like. Endoscopic surgical techniques and procedures are widely known, e.g., endoscopic surgical techniques are disclosed in the following publications which are incorporated by reference: Textbook of Laparoscopy, Jaroslav Hulka, M.D., Grune & Stratton, Inc., New York (1985) and Laparoscopy for Surgeons, Barry A. Salky, M.D., Igaku-Shoin, New York(1990). When utilizing endosurgical techniques, typically a patient is initially anesthetized using a sufficient dose of anesthesia effective to induce an anesthetized state. Conventional anesthesiology techniques and procedures are utilized including, where needed, the use of an endotracheal tube and a ventilator. The initial step after the application of anesthesia is the insufflation of the body cavity containing the target surgical site. This is done using conventional techniques and equipment. The gases which are used include conventional sterile gases such as carbon dioxide. After the body cavity has been insufflated sufficiently so that the surgeon has room to manipulate and maneuver instrumentation within the body cavity, several conventional trocars are inserted through the body cavity wall into the body cavity, for example, the abdominal cavity. Conventional trocars typically comprise a piercing obturator concentrically housed in a trocar cannula. After the trocars are inserted, the piercing obturators are removed from the trocar cannulas leaving the trocar cannula as a pathway to the body cavity. Conventional endoscopic instrumentation is inserted through the cannulas including endoscopes, staplers, sutures, cannulas, electrosurgical instruments, ligating clip appliers, and the like. The instruments are maneuvered to the target surgical site where a surgical procedure is performed. The surgeon views the interior of the body cavity and the target surgical site by observing the output from the endoscope. Conventional endoscopes typically are connected to video cameras and have the output displayed on a video monitor.

One of the crucial endoscopic techniques which must be mastered by the surgeon when utilizing endoscopic surgical procedures, is the ability to maneuver instruments in a three-dimensional body cavity while observing a two-dimensional visual output on the video display of the endoscope. This requires both skill and judgment based upon the experience of having performed previous operations. When using a conventional clip applier, the surgeon must locate the vessel or tissue to be ligated and engage the vessel or tissue in the jaws of the clip applier. Typically, at least two clips are applied by the surgeon to either side of the blood vessel or tissue about the intended cut. Then it is necessary to withdraw the clip applier from the body cavity through a trocar cannula and to reinsert an endoscopic cutting instrument, such as endoscopic scissors, and maneuver the instrument to the ligated blood vessel or tissue. The surgeon then maneuvers the endoscopic cutting instrument in position about the intended cut and then makes the cut in the tissue. As previously mentioned, the physician is maneuvering in a three-dimensional body cavity, however, he only has two-dimensional input from the video display of the endoscope. Therefore, the surgeon must use extreme care in maneuvering the cutting instrument to the ligated tissue or blood vessel where the cut is to be made. Not only is it time consuming to remove a clip applier and insert and maneuver a cutting instrument to complete the ligation procedure, there is also an element of hazard present as the surgeon attempts to maneuver the cutting instrument in the relatively cramped space in the body cavity. The hazards include accidental nicking or cutting of organs or blood vessels or tissue.

Figure 2:
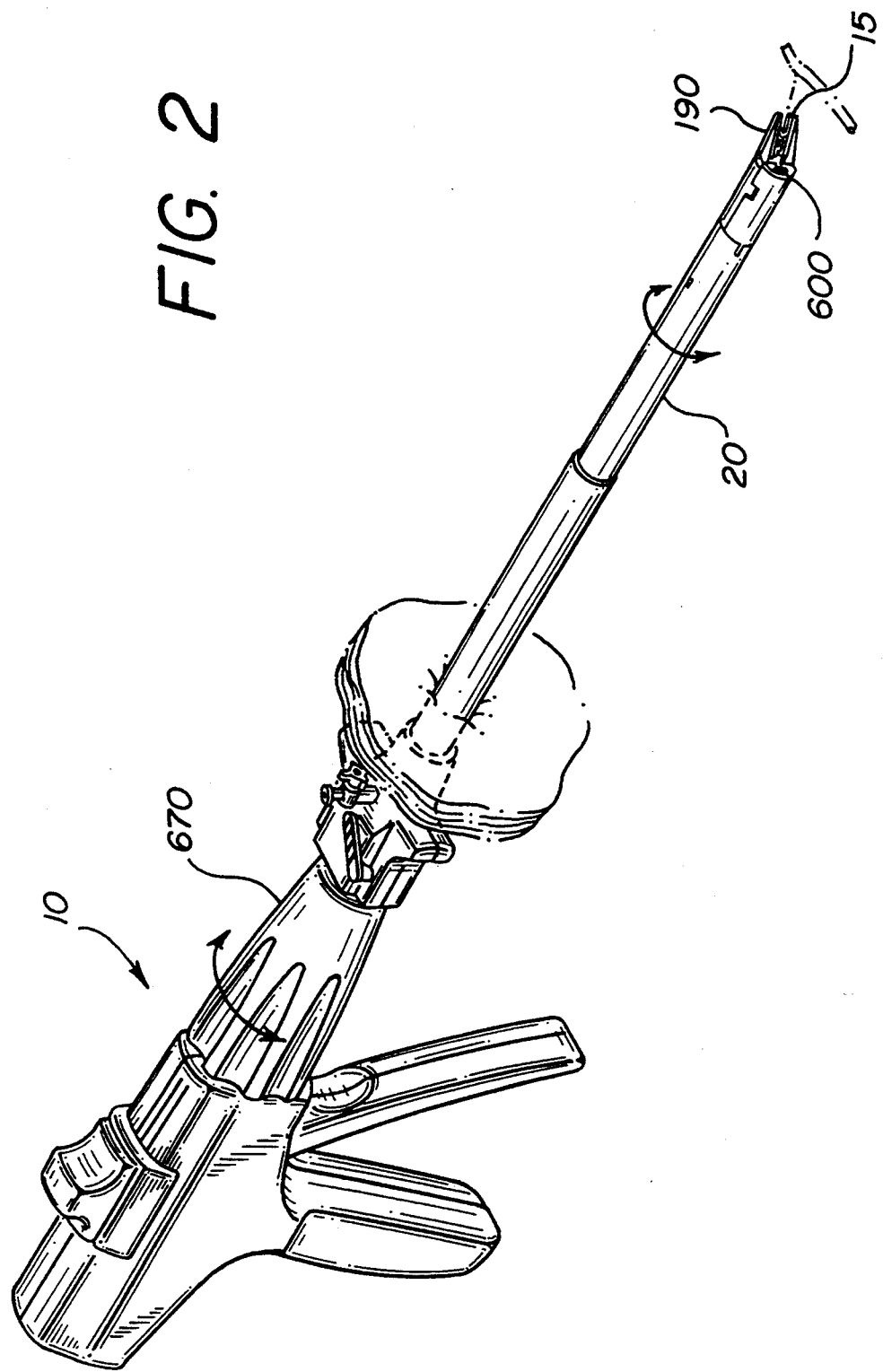
FIG. 2 is a perspective view of the endoscopic ligation and division apparatus of the present invention shown inserted through a trocar and cannula assembly which has been previously inserted into a body cavity.
Figure 3:
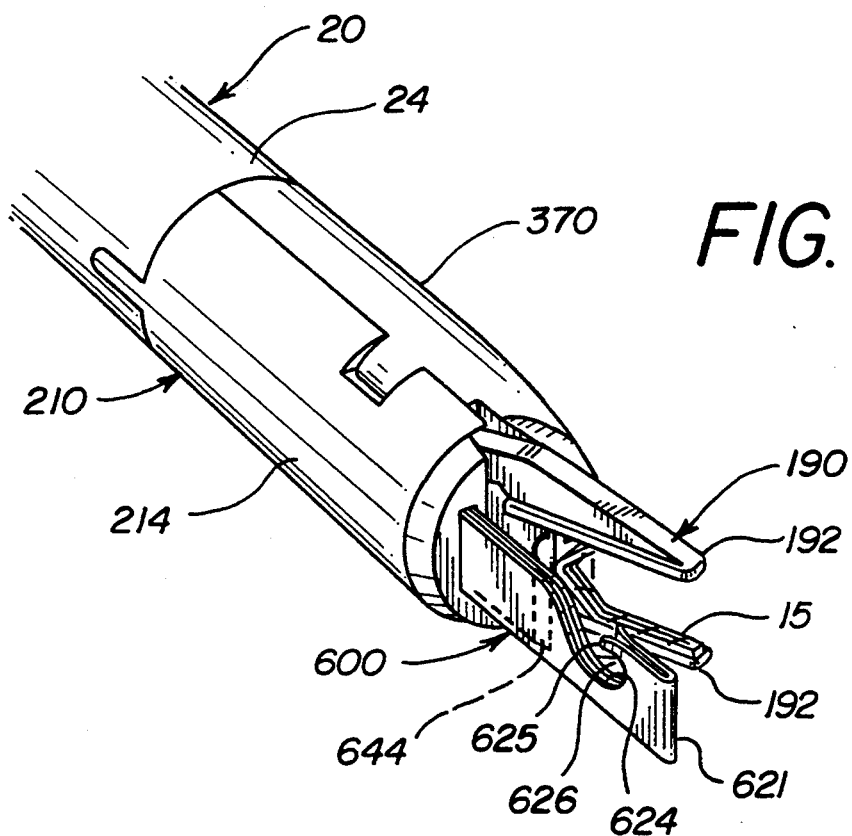
FIG. 3 is an enlarged perspective view of the distal end of the apparatus of FIG. 1 showing the ligation and cutting means.
Figure 4:
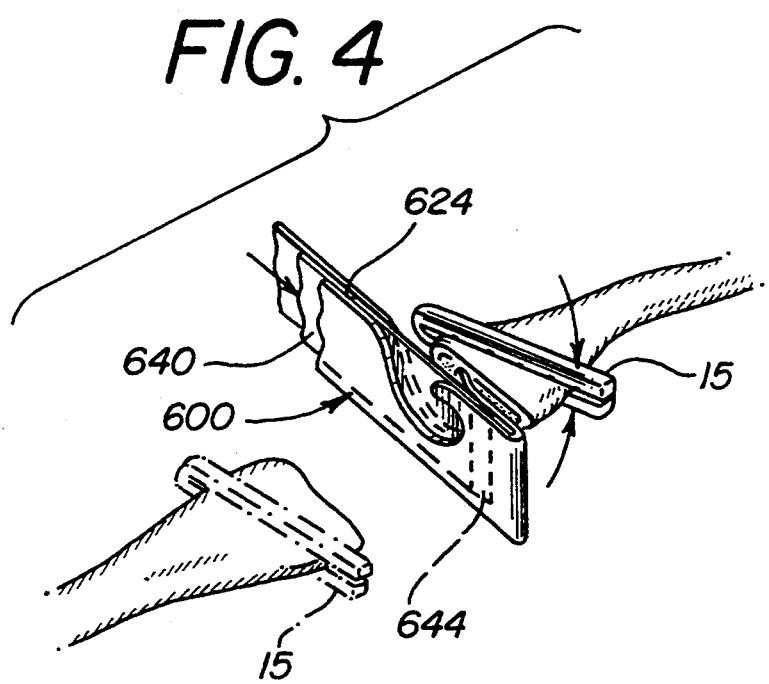
FIG. 4 is a partial perspective of the cutting means after actuating the apparatus.

Using the endoscopic ligation and division apparatus 10 of the present, these deficiencies are eliminated. Referring to FIG. 2, the ligation and division mechanism 10 of the present invention is inserted through a trocar cannula into a body cavity and maneuvered by the surgeon to the target surgical site where a blood vessel or tissue is to be ligated. The ligation and division apparatus 10 is a multiple clip applier having an automatic clip feed. In addition, the apparatus 10 is also a cutter. The surgeon, after positioning the jaw members 192 of the apparatus 10 about the targeted blood vessel or tissue, applies at least one clip 15 to either side of an intended cut in the blood vessel or tissue. This is done by simply squeezing and releasing the trigger assembly 65. After the clips 15 have been applied, the surgeon then extends the cutting mechanism by pushing down on the button 400 and sliding the button 400 and base 510 forward to the maximum distal position so that the isolation hook 625 is completely extended. Next, the physician positions the blood vessel or tissue within the hooked-shaped opening 626 of the isolation hook 625 and then actuates the trigger assembly 65 by squeezing the trigger which causes the blade 644 to travel distally and cut the blood vessel or tissue engaged within the hook-shaped opening 626 of the isolation hook 625. After the tissue or blood vessel is cut, the surgeon retracts the isolation hook 625 by pushing down on the button 400 and sliding base 510 with the button 400 to the proximal-most position and releasing the button. This also causes the cutting mechanism to be deactivated and the forming and feeding mechanisms to be reactivated.

It will be appreciated by those skilled in the art that the ligation and division apparatus 10 can be used not only in endoscopic surgical procedures but also in conventional open procedures. It will also be appreciated that the apparatus 10 may, if one were willing to accept whatever disadvantages maybe present,be inserted through a small slit directly into a body cavity without a conventional trocar.

The following example is illustrative of the principles and practice of the present invention although not limited thereto.

EXAMPLE

A mammal is prepared for surgery using conventional surgical techniques. A sufficient dose of a conventional anesthesia is administered using conventional anesthesiology techniques effective to induce an anesthetized state. The abdominal cavity of the patient is then insufflated using conventional insufflation equipment and techniques with carbon dioxide gas to produce a sufficiently effective pneumoperitoneum. Three trocars are then inserted through the abdominal wall of the mammal into the abdominal cavity. The trocars are conventional trocars having elongated obturators with piercing tips concentrically housed in trocar cannulas. The trocar obturators are then removed leaving the trocar cannulas as pathways to the abdominal cavity. An endoscope is inserted through one of the trocar cannulas. The output from the endoscope is display on a video monitor. The surgeon observes the interior of the abdominal cavity on the video monitor and maneuvers instruments into position using the video monitor display. The ligation and division apparatus 10 of the present invention is inserted through one of the trocar cannulas. The surgeon maneuvers the distal end of the apparatus 10 to a position proximate to a target blood vessel which is to be ligated. The surgeon positions the jaws 192 of the apparatus 10 about the blood vessel and applies two ligating clips 15 on one side of an intended cut. The surgeon then slides the jaws 192 of the apparatus 10 along the blood vessel and applies two ligating clips 15 along the other side of the intended cut. The physician then extends the isolation hook 625 by pressing down on button 400 and sliding the base 510 and button 400 forward to the maximal distal position. This activates the cutting mechanism of the apparatus 10 while simultaneously deactivating the clip forming mechanism. The surgeon then positions the blood vessel 10 within the hook-shaped opening 626 of the isolation hook 625 such that the cut will occur between the two sets of ligating clips 15. The surgeon then actuates the cutting mechanism by squeezing the trigger assembly 65 such that the cutting blade 644 advances distally through the blood vessel contained within the hook-shaped opening 626 of the isolation hook 625. As the surgeon releases the trigger assembly 65, the blade 644 is retracted from the hook-shaped opening 626. The surgeon then retracts the cutting mechanism by pushing down on the button 400 and sliding base 510 and button 400 back to the maximal proximal position. This de-activates the cutting mechanism and re-activates the clip forming mechanism. The surgeon then withdraws the distal end of the apparatus 10 from the body cavity and out through the trocar cannula. The surgeon then removes the trocar cannulas and closes up the wounds using conventional techniques including stapling, suturing, and/or taping.

The endoscopic ligation and division mechanism 10 of the present invention provides a means for cutting and ligating with a single instrument. The surgeon can engage a blood vessel or tissue and apply clips to either side of an intended cut and then cut the tissue or blood vessel without having to remove the ligating apparatus and insert a separate endoscopic cutting apparatus. This improves the efficiency of the surgical procedure by decreasing the amount of time necessary to perform the ligating procedure. In addition, there are benefits to the patient resulting from the decreased time required to perform this surgical procedure and the elimination of the possibility of a separately introduced cutting apparatus damaging or cutting organs or tissue or blood vessels. A single trigger assembly 65 is used to fire both the ligating clip forming mechanism as well as the cutting mechanism. The clutch mechanism 130 deactivates the clip forming mechanism and activates the cutting mechanism when the cutting assembly is extended, and activates the clip forming mechanism and deactivates the cutting mechanism when the cutting assembly is withdrawn. The use of a single trigger to actuate the clip forming mechanism and the cutting mechanism makes the apparatus 10 extremely user friendly in the hands of the trained surgeon.

Although this invention has been shown and described with respect to detailed embodiments thereof, it will be understood by those skilled in the art that various changes in form and detail thereof may be made without departing from the spirit and scope of the claimed invention.

What is claimed is:

1. An endoscopic surgical apparatus comprising:
 a frame;
 a tubular shaft attached to said frame, the tubular shaft having a distal end and a proximal end;
 means for ligating;
 means for cutting;
 a handle attached to said frame;
 trigger means mounted on the frame for actuating the ligating means and cutting means; and,
 clutch means mounted in the frame for switching the trigger means between a first mode for actuating said ligating means and a second mode for actuating said cutting means wherein when said trigger means is in said second mode, said ligating means is incapacitated.

2. The apparatus of claim 1 further comprising feed means attached to said frame for feeding ligating clips to said ligating means.

3. The apparatus of claim 2 wherein said feed means comprise a feed bar driven by the actuation means which feeds a ligating clip from a stack of clips located within said shaft to the ligating means.

4. The apparatus of claim 1 further comprising a timing means which allows loading of a clip only after the jaw members are opened to their maximum width.

5. The apparatus of claim 2 further comprising a plurality of ligating clips contained within the tubular shaft, the clips capable of being fastened to body tissue by said ligating means.

6. The apparatus of claim 5 wherein clips are contained within a clip track mounted within said shaft.

7. The apparatus of claim 1 wherein the shaft is rotatably attached to the frame by rotation means.

8. The apparatus of claim 1 wherein the ligating means comprises a pair of jaw members mounted to said shaft, the jaw members having cam surfaces, said jaw members capable of holding a ligating clip.

9. The apparatus of claim 8 further comprising a cam channel for actuating said jaws.

10. The apparatus of claim 8 wherein said jaws further comprise at least one groove in each jaw member for receiving a ligating clip.

11. The apparatus of claim 10 further comprising mounting means for said jaw members.

12. The apparatus of claim 1 further comprising fluid sealing means mounted in said shaft.

13. The apparatus of claim 1 wherein said clutch means comprises a plate member having cam means extending therefrom, said cam means having at least one cam surface.

14. The apparatus of claim 11 wherein the cam means comprises a ligating engagement cam surface and a ligating disengagement cam surface.

15. The apparatus of claim 1 wherein said actuation means comprises a trigger assembly pivotally mounted in said frame.

16. The apparatus of claim 1 wherein said ligating means comprises a feeder plate and a former plate connected to said actuating means.

17. The apparatus of claim 1 wherein said cutting means comprises a J-hook and a cutting blade extendable from the distal end of said shaft by extension means.

18. The apparatus of claim 17 wherein said J-hook comprises a plate member having a distal hook aperture therein for engaging tissue or blood vessels, said hook having a track in which said cutting blade is moveable.

19. The apparatus of claim 17 wherein said extension means comprises an extension plate slidably mounted in the frame which is actuated by extension actuating means, said extension plate causing the J-hook and cutting blade to be extended from and withdrawn into said shaft and said extension plate interacting with the clutch means to activate and deactivate the ligating means.

20. The apparatus of claim 19 wherein said extension actuating means comprises a button and a slidable base.

21. The apparatus of claim 1 further comprising lockout means mounted in the frame to prevent the ligating means from actuating said jaws after a last clip has been fired.

22. The apparatus of claim 1 further comprising an anti-backup mechanism mounted in the frame to prevent a clip from being partially formed.

23. The apparatus of claim 1 further comprising a lockout means mounted in the frame to prevent the ligating means from actuating said jaws when said cutting means is enabled.

24. The apparatus of claim 1 further comprising a means for deactivating said cutting means when said ligating means is enabled.

25. A method of ligating and cutting mammalian tissue or blood vessels comprising:
inserting the distal end of an endoscopic surgical apparatus into the body cavity of a mammal, wherein the apparatus comprises:
a frame;
a tubular shaft attached to said frame, the tubular shaft having a distal end and a proximal end;
means for ligating;
means for cutting;
a handle attached to said frame;
trigger means mounted to the frame for actuating the ligating means and cutting means; and,
clutch means mounted in the frame for switching the trigger means between a first mode for actuating said ligating means and a second mode for actuating said cutting means;
applying at least one ligating clip to the tissue or blood vessel;
using the clutch means to switch the actuating means to a cutting mode;
engaging said tissue or blood vessel in said cutting means; and,
actuating the cutting means to cut said tissue or blood vessel.

26. The method of claim 25 further comprising feeding ligating clips to said ligating means.

27. The method of claim 25 further comprising using a timing means which allows loading of a clip only after the ligating means is opened to its maximum width.

28. The method of claim 25 further comprising fastening a plurality of ligating clips to body tissue.

29. (Amended) The method of claim 25 further comprising rotating the shaft using rotation means.

30. The method of claim 25 further comprising using fluid sealing means mounted in said shaft.

31. The method of claim 25 further comprising a trigger assembly pivotally mounted in said frame as actuation means.

32. The method of claim 25 further comprising using as cutting means a J-hook and a cutting blade extendable from the distal end of said shaft by extension means.

33. The method of claim 32 wherein said J-hook comprises a plate member having a distal hook aperture attached thereto for engaging tissue or blood vessels, said hook having a track in which said cutting blade is moveable.

34. The method of claim 25 wherein the apparatus further comprises an anti-backup mechanism to prevent a clip from being partially formed.

35. The method of claim 25 further comprising using a lockout means to prevent the actuating means from actuating said ligating means when said cutting means is enabled.

36. The method of claim 25 further comprising using a lockout means to deactivate said cutting means when said ligating means is enabled.

* * * * *

UNITED STATES PATENT AND TRADEMARK OFFICE
CERTIFICATE OF CORRECTION

PATENT NO. : 5,447,513
DATED : September 5, 1995
INVENTOR(S) : Mark A. Davison, et. al.

It is certified that error appears in the above-indentified patent and that said Letters Patent is hereby corrected as shown below:

Column 18, Line 32 - "11" should be "13"

Column 18, Line  3 - "1" should be "8"

Signed and Sealed this

Seventeenth Day of December, 1996

*Attest:*

BRUCE LEHMAN

*Attesting Officer*    Commissioner of Patents and Trademarks